US010209219B2

(12) United States Patent
Burton et al.

(10) Patent No.: US 10,209,219 B2
(45) Date of Patent: Feb. 19, 2019

(54) BACKGROUND PEAK MONITORING FOR ION MOBILITY SPECTROMETRY

(75) Inventors: Julian C. Burton, Morristown, NJ (US); Reno F. DeBono, Morristown, NJ (US)

(73) Assignee: SMITHS DETECTION MONTREAL INC., Laval (CA)

( * ) Notice: Subject to any disclaimer, the term of this patent is extended or adjusted under 35 U.S.C. 154(b) by 1368 days.

(21) Appl. No.: 13/881,823

(22) PCT Filed: Oct. 27, 2011

(86) PCT No.: PCT/US2011/058050
§ 371 (c)(1),
(2), (4) Date: Jul. 16, 2013

(87) PCT Pub. No.: WO2012/058407
PCT Pub. Date: May 3, 2012

(65) Prior Publication Data
US 2013/0297227 A1 Nov. 7, 2013

Related U.S. Application Data

(60) Provisional application No. 61/407,335, filed on Oct. 27, 2010, provisional application No. 61/407,327, (Continued)

(51) Int. Cl.
B01D 59/44 (2006.01)
G01N 27/62 (2006.01)
(Continued)

(52) U.S. Cl.
CPC .......... G01N 27/622 (2013.01); G01N 23/00 (2013.01); G06K 9/0053 (2013.01);
(Continued)

(58) Field of Classification Search
USPC .................... 702/27; 250/282, 286
See application file for complete search history.

(56) References Cited

U.S. PATENT DOCUMENTS 6,291,821 B1 * 9/2001 Danylewych-May ...................... G01N 25/56
250/286
6,822,222 B2 * 11/2004 Hayek ................ H01J 49/0036
250/281
(Continued)

FOREIGN PATENT DOCUMENTS

WO 01/93308 12/2001
WO 2012056322 5/2012
WO 2012058406 5/2012

OTHER PUBLICATIONS

Anonymous, Quantum Sniffer QS-H150 Explosives Detector, Implant Sciences Corporation Product Information, 2008, 2 pages.
(Continued)

Primary Examiner — Lam Nguyen
(74) Attorney, Agent, or Firm — Casimir Jones SC; David W. Staple

(57) ABSTRACT

Method and systems for monitoring ion mobility spectrometers are provided. The method can include acquiring scan data, and generating a segment data set from the scan data. The method can further include deriving a subset of peak data from the segment data, where the subset of peak data has an associated set of peak metrics, and deriving a value from the subset of peak data associated with a criteria element of the associated set of peak metrics, where the criteria element has an associated range of values. The method can further include providing an indication in the event the value lies outside the associated range of values.

20 Claims, 14 Drawing Sheets

Related U.S. Application Data filed on Oct. 27, 2010, provisional application No. 61/407,342, filed on Oct. 27, 2010.

(51) Int. Cl.
*H01J 49/00* (2006.01)
*G06K 9/00* (2006.01)
*H01J 49/02* (2006.01)
*H01J 49/06* (2006.01)
*G01N 23/00* (2006.01)
*H01J 49/04* (2006.01)

(52) U.S. Cl.
CPC ........ *H01J 49/0031* (2013.01); *H01J 49/025* (2013.01); *H01J 49/04* (2013.01); *H01J 49/06* (2013.01); *H01J 49/061* (2013.01)

(56) References Cited

U.S. PATENT DOCUMENTS

| | | |
|---|---|---|
| 2005/0253061 A1 | 11/2005 | Cameron et al. |
| 2013/0284914 A1 | 10/2013 | Zaleski et al. |
| 2013/0298938 A1 | 11/2013 | Bian et al. |

OTHER PUBLICATIONS

International Search Report and Written Opinion for PCT/US2011058050, dated Mar. 8, 2012, 12 pages.

\* cited by examiner

BACKGROUND PEAK MONITORING FOR ION MOBILITY SPECTROMETRY

CROSS-REFERENCE TO RELATED APPLICATIONS

This application claims priority to U.S. Provisional Patent Application Ser. No. 61/407,342, filed Oct. 27, 2010, U.S. Provisional Patent Application Ser. No. 61/407,327, filed Oct. 27, 2010, and U.S. Provisional Patent Application Ser. No. 61/407,335, filed Oct. 27, 2010, each of which is incorporated by reference in its entirety.

FIELD OF THE INVENTION

This application is directed to monitoring ion mobility spectrometers.

BACKGROUND OF THE INVENTION

Ion mobility spectrometry is a method used to identify the composition of a sample of ions using ion mobility. Ion mobility spectrometers can be employed at security checkpoints, such as airports, to assist in the detection of explosives and narcotics. When used at airports, for example, residue from luggage can be transferred to a swab, which can be manipulated so that molecules and/or atoms associated with the residue pass into an ionization region within the ion mobility spectrometer. In the ionization region, the molecules and atoms associated with the residue can be ionized. Both positive and negative ions can form in the ionization region. An electric field at grids spaced between the ionization region and a drift region can be pulsed to allow ions to pass from the ionization region into the drift region. The ions in the drift region can be further subject to a force as a result of an electric field maintained in the drift region. Once in the drift region, the ions can separate based upon the ions' respective ion mobility. In this way, a time-of-flight measurement of the ions in the drift region (which can be measured as a change in current magnitude on a collector plate at one end of the drift region), can provide an identifying peak in a measured current magnitude, and which can be associated with a particular ion. The plot of current magnitude at the collector as a function of time is referred to as a plasmagram.

SUMMARY OF THE INVENTION

In one aspect, embodiments can provide a method of monitoring. The method can include acquiring scan data and generating a segment data set from the scan data. The method can further include deriving a subset of peak data from the segment data, wherein the subset of peak data has an associated set of peak metrics, and deriving a value from the subset of peak data associated with a criteria element of the associated set of peak metrics, wherein the criteria element has an associated range of values. In addition, the method can include providing an indication in the event the value lies outside the associated range of values.

In another aspect, embodiments can provide a further method of monitoring. The method can include acquiring scan data, generating a segment data set from the scan data, and utilizing a set of peak metrics to determine a range of values associated with a criteria element of the set of peak metrics. The method can further include determining a range of segment drift time values associated with the range of values, and providing an indication where analysis of a subset of the segment data corresponding to the range of segment drift time values does not yield a value corresponding to the range of values.

In an additional aspect, embodiments can provide an ion mobility spectrometer analysis system. The ion mobility spectrometer analysis system can include a collector interface coupled to a collector and a processor. The processor can be configured to acquire scan data from the collector interface, generate a segment data set from the scan data, and derive a subset of peak data from the segment data, wherein the subset of peak data has an associated set of peak metrics. The processor can further be configured to derive a value from the subset of peak data associated with a criteria element of the associated set of peak metrics, wherein the criteria element has an associated range of values, and wherein the ion mobility spectrometer analysis system is configured to provide an indication in the event the value lies outside the associated range of values.

In yet a further aspect, embodiments can provide a further ion mobility spectrometer analysis system. The ion mobility spectrometer analysis system in this aspect can include a collector interface coupled to a collector and a processor. The processor in this aspect can be configured to acquire scan data from the collector interface, generate a segment data set from the scan data, utilize a set of peak metrics to determine a range of values associated with a criteria element of the set of peak metrics, and determine a range of segment drift time values associated with the range of values. The ion mobility spectrometer analysis system in this aspect can further be configured to provide an indication to a user in the event that analysis of a subset of the segment data corresponding to the range of segment drift time values does not yield a value corresponding to the range of values.

In yet another aspect, embodiments can provide a computer-readable medium comprising instructions stored thereon, where the instructions, responsive to being executed by a processor, can cause the processor to perform a method. In this aspect, the method can include acquiring scan data, generating a segment data set from the scan data, deriving a subset of peak data from the segment data wherein the subset of peak data has an associated set of peak metrics, and deriving a value from the subset of peak data associated with a criteria element of the associated set of peak metrics, wherein the criteria element has an associated range of values. The processor can be associated with an ion mobility spectrometer analysis system that is configured to provide an indication in the event the value lies outside the associated range of values.

In a further aspect, embodiments can provide for a further computer-readable medium comprising instructions stored thereon, where the instructions, responsive to being executed by a processor, can cause the processor to perform a method. In this aspect, the method can include acquiring scan data, generating a segment data set from the scan data, utilizing a set of peak metrics to determine a range of values associated with a criteria element of the set of peak metrics, determining a range of segment drift time values associated with the range of values. The processor can be associated with an ion mobility spectrometer analysis system that is configured to provide an indication in the event that analysis of a subset of the segment data that corresponds to the range of segment drift time values does not yield a value that corresponds to the range of values.

Additional features and embodiments will be set forth in part in the description which follows, and in part will be understood from the description, or may be learned from the description. It is to be understood that both the foregoing general description and the following detailed description are exemplary and explanatory only and are not restrictive of the claimed subject matter.

BRIEF DESCRIPTION OF THE DRAWINGS

The accompanying drawings, which are incorporated in and constitute a part of this specification, illustrate exemplary embodiments and together with the description, serve to explain the principles of the disclosure.

DETAILED DESCRIPTION OF THE INVENTION

Reference will now be made in detail to the disclosed embodiments of the disclosure, examples of which are illustrated in the accompanying drawings. Wherever possible, the same reference numbers will be used throughout the drawings to refer to the same or like parts.

Figure 1:
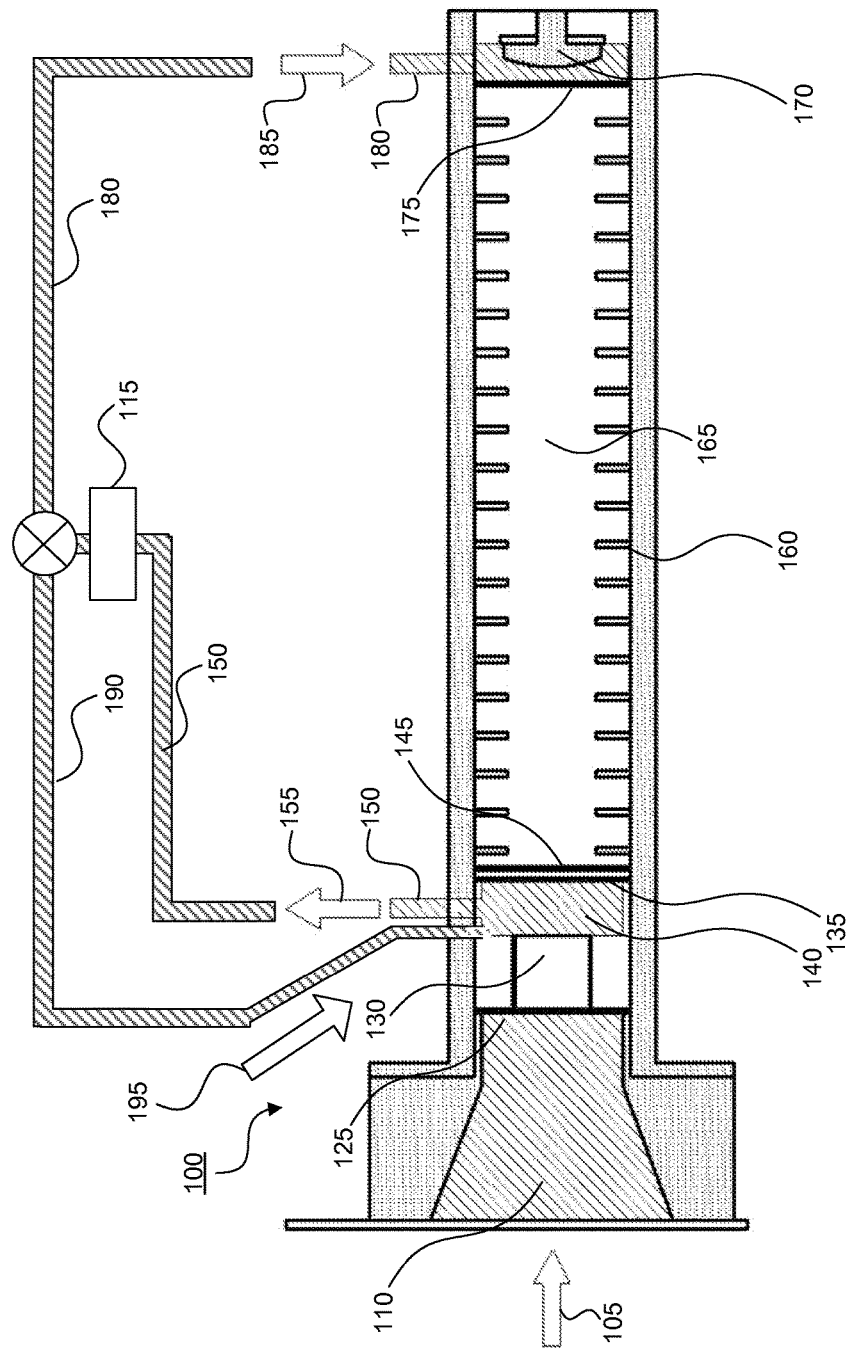
FIG. 1 is a cross-sectional view of an ionization region and a drift region of an ion mobility spectrometer consistent with an embodiment.

A portion of an ion mobility spectrometer 100 consistent with an embodiment is depicted in FIG. 1. Molecules and/or atoms associated with a sample being tested can enter through an inlet 110 (depicted with arrow 105). Sample molecules and/or atoms then pass a repelling grid 125 into an ionization region 140. The repelling grid 125 can comprise inert metal (e.g., gold-plated nickel), and can have a grid spacing of about 0.1 mm. The ionization region 140 can include a region with an ionization source 130. The ionization source 130 can comprise a material such as Nickel-63. Alternatively, ions can be created in the ionization region 140 as a result of corona discharge ionization, photoionization, electrospray ionization, matrix assisted laser desorption ionization (MALDI), or the like.

The ion mobility spectrometer 100 can operate in positive ion mode and negative ion mode. In these modes, certain components of the ion mobility spectrometer 100 can exhibit voltages in order to create an electric field along the length of the ion mobility spectrometer 100. When the ion mobility spectrometer 100 is operating in positive ion mode, for example, the repelling grid 125 can exhibit a relatively high positive voltage. As described further below, when operating in positive ion mode, other components of the ion mobility spectrometer 100 located towards the opposite end of the ionization region 140 and across the drift region 160 will exhibit lower voltages. This configuration will create an electric field in the ionization region 140, for example, that directs positive ions away from the inlet 110. In an embodiment, the magnitude of the positive voltage on the repelling grid 125 can be about 2100 V. The range of magnitudes of the positive voltage on the repelling grid 125 can be 1000V to 5000V. Example values can be higher or lower depending upon the physical dimensions of the system. Both a fixed grid 135 and a gating grid 145 are located between the ionization region 140 and the drift region 165. As discussed above, and in positive ion mode, the fixed grid 135 can exhibit a voltage that is less than the positive voltage on the repelling grid 125 such that there is a potential gradient (i.e., an electric field) oriented across the ionization region 140. Other components can also be present between the repelling grid 125 and the fixed grid 135 in the ionization region 140 in support of an electric field in the ionization region 140. In an embodiment, when the voltage on the repelling grid 125 is approximately 2100 V as described above, the fixed grid 135 can exhibit a positive voltage that is approximately 1810 V. The voltage on the fixed grid 135 can be chosen so the potential gradient near the fixed grid 135 in the ionization region 140 and near the fixed grid 135 in the drift region 165 will provide a force on ions that will direct the ions from the ionization region 140 to the drift region 165 when the gating grid 145 is "open" (as is described further below). By way of example only, and without limitation, a configuration that allows for a uniform electric field across the barrier between the ionization region 140 and the drift region 165 is a configuration that can provide a uniform force on an ion to direct ions (of one polarity) from the ionization region 140 to the drift region 165. According to the above embodiment, an electric field across the ionization region 140 can have a magnitude that ranges from 50 V/cm to 500 V/cm. The electric field in the ionization region 140 does not need to be uniform throughout the ionization region 140. However, the electric field in the drift region 165 can be generally uniform. For example, where the drift region 165 is approximately 6.9 cm, and the electric field across the drift region 165 also has a magnitude of 250 V/cm, the voltage on a guard grid 175 at one end of the drift region 165 can be approximately 90 V. In other embodiments, the range of values for an electric field in the drift region 165 can be 200 V/cm to 300 V/cm.

Adjacent to the fixed grid 135 is the gating grid 145, where the gating grid 145 can be positioned so the fixed grid 135 is between the repelling grid 125 and the gating grid 145. The gating grid 145 can be approximately 0.75 mm from the fixed grid 135. A shutter structure consistent with the combination of the fixed grid 135 and the gating grid 145 is referred to as a Bradbury-Nielsen gate. (Without limitation, another shutter structure consistent with the present disclosure is a Tyndall's gate.) The combination of the fixed grid 135 and the gating grid 145 can comprise two sets of parallel wires (which can be two etched foils), where the spacing between the wires of the respective grids can be about 0.8 mm. The parallel wires on the grids can be oriented in the same direction, but can be spaced so that, when viewed from a direction that is perpendicular to the plane of the grid, the wires are interleaved. There can also be an insulating foil of thickness about 0.75 mm between the grids. The fixed grid 135 and the gating grid 145 can comprise Invar or other materials. In positive ion mode, the gating grid 145 can be kept at a higher voltage than the fixed grid 135 to create a barrier along the potential gradient between the ionization region 140 and the drift region 165. When the gating grid 145 is at a higher potential than the fixed grid 135, the gating grid 145 is referred to as "closed." The difference in voltage between the gating grid 145 and the fixed grid 135, when the gating grid 145 is closed, can be about 20 V. The voltage of the gating grid 145 can have a magnitude of about 1830 V in positive ion mode. Such a magnitude can have the effect of introducing an electric field that interferes with the passage of positive ions from the ionization region 140 through the drift region 165 to a collector 170 (described further below).

After molecules and/or atoms have entered the ionization region 140 and positive ions form, the repelling grid 125 can be maintained at a high voltage as described above and the gating grid 145 can remain closed for approximately 20 milliseconds. After this time period elapses, a negative voltage pulse can be applied to the gating grid 145 to open the gating grid 145 and allow positive ions to move from the ionization region 140 to the drift region 165 so the positive ions may travel toward the collector 170. In an embodiment, when the gating grid 145 is approximately 20 V higher than the fixed grid 135 when closed, the negative voltage pulse to the gating grid 145 can have an amplitude of approximately 25 V to open the gating grid 145. In an embodiment, the negative voltage pulse applied to the gating grid 145 to open the gating grid 145 can have an amplitude so the potential gradient at the boundary between the ionization region 140 and the drift region 165 directs positive ions from the ionization region 140 to the drift region 165 so positive ions can arrive at the collector 170. A time period permitted for the ions to move from the ionization region 140 to the drift region 165 (when the gating grid 145 is open) can be about 200 microseconds. The gating grid 145 can be open for about 200-300 microseconds, but can be open for as short as about 50 microseconds and open for as long as about 1000 microseconds. Opening the shutter structure (such as by pulsing the voltage on the gating grid) for this duration, and then closing the shutter structure can allow positive ions to move into the drift region 165 so the positive ions can arrive at the collector 170. In the drift region 165, an electric field can provide a force on the positive ions to direct the positive ions through the drift region 165 towards the guard grid 175 and the collector 170. The collector 170 can be any suitable structure for detecting pulses of current associated with moving ions, such as a Faraday plate. As the positive ions move through the drift region 165 towards the collector 170, the positive ions can move through a drift gas. In an embodiment, the drift gas can move in the opposite direction to the flow of the positive ions, where the flow of positive ions is towards the collector 170. The drift gas can enter the drift region 165 from a drift flow 180 (indicated by arrow 185) and exit the ion mobility spectrometer 100 through an exhaust flow 150 (indicated by arrow 155). The drift gas in the drift region 165 can be dry air, although other gases such as nitrogen or helium can be used. As the ions move through the drift region 165 toward the collector 170, the various species of ions can separate as a function of their mobility. The drift time of the ions across the drift region 165 can vary, depending on their atomic and molecular characteristics and the temperature and pressure of the drift gas. For a drift region 165 that is approximately 6.9 cm in length and at normal atmospheric pressure and temperature, the drift time can be in the range of 5 milliseconds to 20 milliseconds. Furthermore, the time period during which data is acquired from the collector 170 associated with one scan can range from about 2 milliseconds to about 40 milliseconds. In an embodiment, one scan can represent a 25 millisecond time period.

Accordingly, electric current values can be measured at regular time intervals at the collector 170, corresponding to time-of-flight signatures of the ionic species that can make up the positive ions present in the drift region 165. As discussed above, in an embodiment, the drift gas can flow in the opposite direction from the movement of the positive ions being measured at the collector 170 in positive ion mode. Such a drift gas flow can be used to keep the drift gas pure, but a flow is not required for operation of the ion mobility spectrometer 100. Other methods and systems for maintaining drift gas purity can include placing sorbent material within the drift region 165.

In an embodiment, as described above, the voltage difference between the gating grid 145 and the guard grid 175 can be approximately 1720 V and the distance between the gating grid 145 and the guard grid 175 can be 6.9 cm. The magnitude of the voltage of the guard grid 175 can be approximately 90 V.

Drift rings 160 can be employed in the drift region 165. In an embodiment, the drift rings 160 can be flat metal rings, spaced at regular intervals between the gating grid 145 and the guard grid 175 and can be biased at equal voltage steps to improve uniformity of the potential gradient (that is, the uniformity of the electric field) within the drift region 165.

Operation of the ion mobility spectrometer 100 in negative ion mode is similar, in principle, to its operation in positive ion mode. The relative voltages on the repelling grid 125, the fixed grid 135, the gating grid 145, and the guard grid 175, however, are inverted. Specifically, the repelling grid 125 can be more negative than the fixed grid 135, which can be more negative than the guard grid 175. In an embodiment of the ion mobility spectrometer 100 operating in negative ion mode, the magnitude of the voltages associated with the repelling grid 125, the fixed grid 135, the gating grid 145, and the guard grid 175 can be approximately similar in magnitude but with opposite polarity to those recited above in positive mode. Specifically, the repelling grid 125 can be approximately −2100 V, the fixed grid 135 can be approximately −1810 V, the guard grid 175 can be approximately −90 V, and the gating grid 145 can be approximately −1830 V when closed, and pulsed to approximately −1805 V when open. The voltage across the drift rings 160 can also be inverted from the circumstance described in positive ion mode to form a uniform potential gradient through the drift region 165. In this way, the potential gradient in negative ion mode is inverted from the potential gradient described above in connection with positive ion mode, thereby inverting the direction of the electric field across the ionization region 140 and the drift region 165 of the ion mobility spectrometer 100.

As described above, the drift region 165 can have an electric field applied along its length, and the slope of the potential field as a function of distance (e.g., the direction of the electric field associated with the potential gradient) can be positive or negative depending on the charge of the ions. Ions of a similar polarity can move from the ionization region 140 into the drift region 165 by the opening and closing of the gating grid 145. The time period of a scan of a collection of ions in the drift region 165 is the time period between when the gating grid 145 opens to admit ions into the drift region 165 from the ionization region 140, and the subsequent opening of the gating grid 145 to admit additional ions into the drift region 165 from the ionization region 140. The interval between subsequent voltage pulses applied to gating grid 145 so that it opens (e.g., negative voltage pulses for operation in positive ion mode and positive voltage pulses for operation in negative ion mode) is referred to as the "scan period." Current measurements that are acquired from the collector 170 from several subsequent scans can be co-added together to improve signal-to-noise of the mobility spectrum reflected in the scans. This collection of data is referred to as a "segment." Data associated with one segment can be acquired in less than a second (e.g., data associated with one segment can be acquired by co-adding approximately 40 scans or less, where the scans have a duration of approximately 25 milliseconds). A series of sequential segments, with characteristic ion peak patterns, can be obtained and can be displayed either as a series of individual segments versus desorption time in seconds (a three-dimensional plasmagram) or as an average of all segments obtained during the analysis (a two-dimensional plasmagram). The desorption time is the time associated with the desorption of molecules and atoms from the swab, such as through the application of heat. The desorption of the molecules and atoms from the swab through the application of heat, for example, can make the molecules and atoms available to pass through the inlet 110 and into the ionization region 140.

As described above, in positive ion mode, the gating grid 145 can be kept at a higher voltage than the fixed grid 135 to create a barrier along the potential gradient between the ionization region 140 and the drift region 165. When the gating grid 145 is at a higher potential than the fixed grid 135, the gating grid 145 is referred to as "closed." Further, as described above, the difference in voltage between the gating grid 145 and the fixed grid 135, when the gating grid 145 is closed, can be about 20 V. Such a magnitude can have the effect of supporting an electric field that interferes with the passage of positive ions from the ionization region 140 through the drift region 165 to the collector 170. Moreover, a negative voltage pulse can be applied to the gating grid 145 to open the gating grid 145 and allow positive ions to move from the ionization region 140 to the drift region 165 so the positive ions may travel toward the collector 370. In an embodiment, when the gating grid 145 is approximately 20 V higher than the fixed grid 135 when closed, the negative voltage pulse to the gating grid 145 can have an amplitude of approximately 25 V to open the gating grid 145. In a further embodiment, a positive voltage pulse of approximately 25 V can be applied to the fixed grid 135, while the gating grid 145 is left unchanged in order to "open" the shutter structure associated with the combination of the fixed grid 335 and the gating grid 345 in positive ion mode. That is, in a further embodiment, and rather than applying a negative voltage pulse to the gating grid 145 while the fixed grid 135 is left unchanged, a positive voltage pulse can be applied to the fixed grid 135 while the gating grid 145 is left unchanged. Further still, in further embodiments, a positive voltage pulse of approximately N volts can be applied to the fixed grid 135 and a negative voltage pulse of approximately 25−N volts can be applied to the gating grid 145 in order to "open" the shutter structure associated with the combination of the fixed grid 135 and the gating grid 145 in positive ion mode.

Further still, and as described above, in negative ion mode, the gating grid 145 can be kept at a lower voltage than the fixed grid 135 to create a barrier along the potential gradient between the ionization region 140 and the drift region 165. When the gating grid 145 is at a lower potential than the fixed grid 135, the gating grid 145 is referred to as "closed." Further, as described above, the difference in voltage between the gating grid 145 and the fixed grid 135, when the gating grid 145 is closed, can be about 20 V. Again, such a magnitude can have the effect of supporting an electric field that interferes with the passage of negative ions from the ionization region 140 through the drift region 165 to the collector 170. Further still, a positive voltage pulse can be applied to the gating grid 145 to open the gating grid 145 and allow negative ions to move from the ionization region 140 to the drift region 165 so the negative ions may travel toward the collector 170. In an embodiment, when the gating grid 145 is approximately 20 V lower than the fixed grid 135 when closed, the positive voltage pulse to the gating grid 145 can have an amplitude of approximately 25 V to open the gating grid 145. In a further embodiment, a negative voltage pulse of approximately 25 V can be applied to the fixed grid 135, while the gating grid 145 is left unchanged in order to "open" the shutter structure associated with the combination of the fixed grid 135 and the gating grid 145 in negative ion mode. That is, in a further embodiment, and rather than applying a positive voltage pulse to the gating grid 145 while the fixed grid 135 is left unchanged, a negative voltage pulse can be applied to the fixed grid 135 while the gating grid 145 is left unchanged. In further embodiments, a negative voltage pulse of approximately N volts can be applied to the fixed grid 135 and a positive voltage pulse of approximately 25−N volts can be applied to the gating grid 145 in order to "open" the shutter structure associated with the combination of the fixed grid 135 and the gating grid 145 in negative ion mode.

Figure 2:
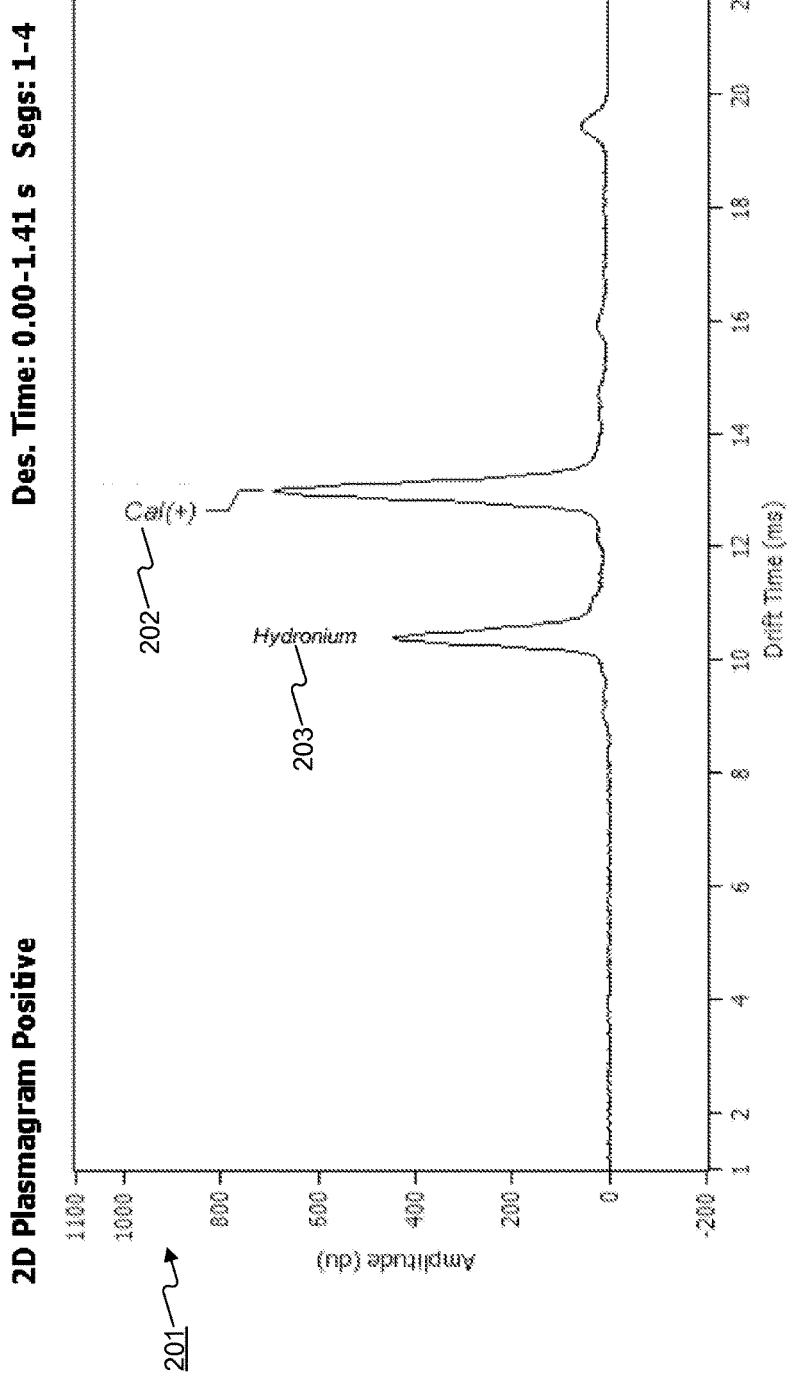
FIG. 2 depicts an example two-dimensional plasmagram associated with a first set of segment measurements of a blank swab in positive ion mode.
Figure 3:
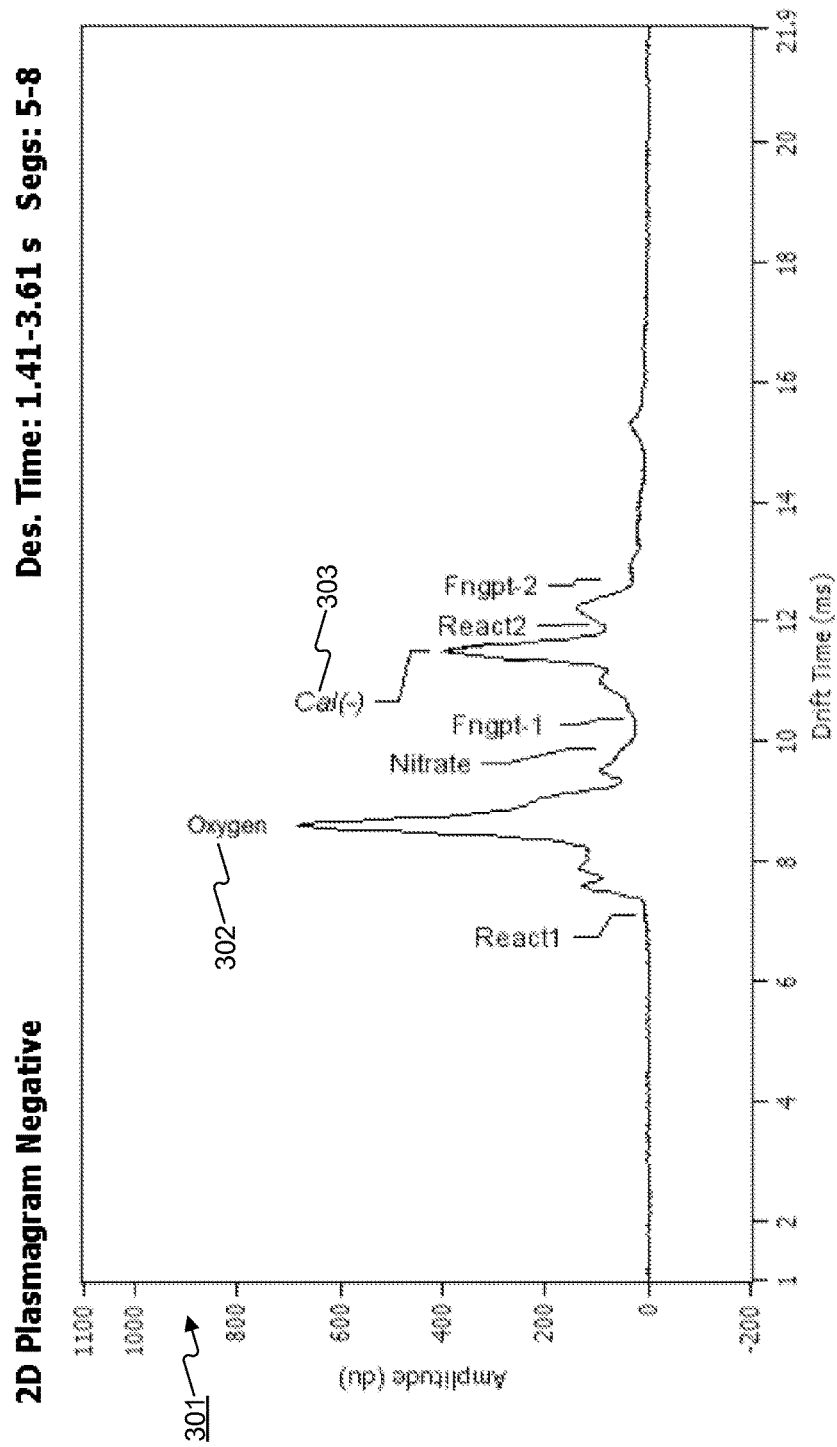
FIG. 3 depicts an example two-dimensional plasmagram associated with a second set of segment measurements of a blank swab in negative ion mode in which reactant has not been introduced into the ionization region.
Figure 4:
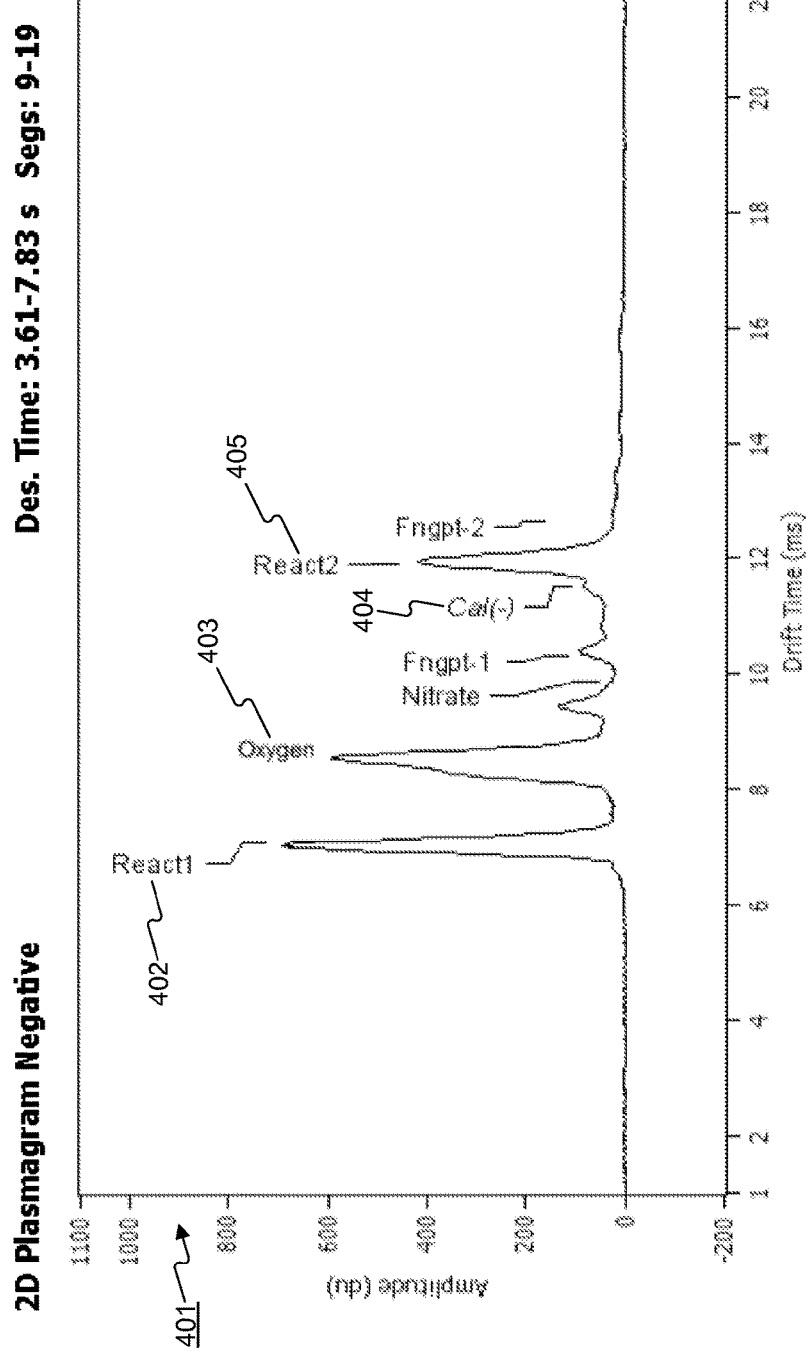
FIG. 4 depicts an example two-dimensional plasmagram associated with a third set of segment measurements of a blank swab in negative ion mode in which reactant has been introduced into the ionization region.

FIGS. 2-4 depict example plasmagrams associated with the current values measured at the collector 170. FIG. 2 is an example two-dimensional plasmagram 201 associated with an ion mobility spectrometer, such as ion mobility spectrometer 100, operating in positive ion mode. The abscissa of the two-dimensional plasmagram 201, the drift time, is the amount of time after the gating grid 145 opens to allow ions into the drift region 165 so that the ions can arrive at the collector 170. That is, when the ion mobility spectrometer 100 is operating in positive ion mode, the zero of the drift time abscissa corresponds to the negative voltage pulse that opens the gating grid 145. The ordinate of the two-dimensional plasmagram 201 is the current signal acquired at the collector 170 as a function of the drift time. The units associated with the ordinate of the two-dimensional plasmagram 201 can be arbitrary, as the measured current at the collector 170 can be a function of a number of design parameters associated with the construction and operation of the ion mobility spectrometer 100. As described above, a plurality of scans can be co-added together to form a segment. In the two-dimensional plasmagram 201 depicted in FIG. 2, each scan in the plurality of scans that make up a segment occurs for at least 21.9 milliseconds, and the segments numbered 1 through 4 (all in positive ion mode and occurring over 1.41 seconds of desorption time) are averaged together. Two peaks are visible in FIG. 2: a nicotinamide peak 202 (labeled in FIG. 2 as "Cal(+)") and a hydronomium peak 203. The occurrence of the nicotinamide peak 202 and the hydronium peak 203 in the two-dimensional plasmagram 201 is discussed below.

Reactants can assist in the creation of positive and negative ions in the ionization region 140. For example, in air, which can contain a small admixture of water vapor, hydronium ions H+(H2O)n (which can also be referred to as hydrated protons or protonated water) can be dominant reactant ions. These ions can form very quickly in the ionization region 140. Sample molecules (e.g., molecule A) can interact with these reactant ions and a third body X according to the following proton transfer reaction:

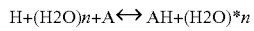

H+(H2O)n+A ↔ AH+(H2O)*n

AH+(H2O)*n+X ↔ AH+(H2O)n−1+H2O+X where the excitation energy can be transferred to third body X, added as a dopant. In the positive ion mode this dopant X can be nicotinamide. In FIG. 2, the presence of nicotinamide as a dopant in positive ion mode is reflected in nicotinamide peak 202 (labeled in the two-dimensional plasmagram 201 as "Cal(+)"). Further, the presence of hydronium is reflected in the hydronium peak 203. With reference to FIG. 1, calibrants and reactants can be introduced through flow 190 (with the direction of flow depicted with arrow 195) from appropriate reservoirs (not shown). Air Purification Cartridge 115 lies between exhaust flow 150 and the drift flow 180 and the flow 190.

FIG. 3 is an example two-dimensional plasmagram 301 associated with the ion mobility spectrometer 100 operating in negative ion mode. As with FIG. 2, the abscissa of the two-dimensional plasmagram 301, the drift time, is the amount of time after the gating grid 145 opens to allow ions into the drift region 165. Note, however, that when the ion mobility spectrometer 100 is operating in negative ion mode, the zero of the drift time abscissa corresponds to the positive voltage pulse that opens the gating grid 145. Again, the ordinate of the two-dimensional plasmagram 301 is the current signal acquired at the collector 170 as a function of the drift time according to the same units associated with FIG. 2. Again, as described above, a plurality of scans can be co-added together to form a segment, and again, as described in connection with FIG. 2, each scan in the plurality of scans that make up a segment in the two-dimensional plasmagram 301, occurs for at least 21.9 milliseconds, and the segments numbered 5 through 8 (all in negative ion mode and occurring between 1.41 seconds and 3.61 seconds of desorption time) are averaged together. Several peaks are visible in FIG. 3, including an oxygen peak 302 and a nitrobenzonitrile peak 303 (labeled in FIG. 3 as "Cal(−)"). Oxygen peak 302 can be a result of the reaction:

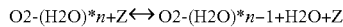

O2-(H2O)*n+Z ↔ O2-(H2O)*n−1+H2O+Z where third body Z can be dopant 4-nitrobenzonitrile. The peak associated with nitrobenzonitrile is labeled "Cal(−)" in FIG. 3, where nitrobenzonitrile can be a dopant in negative mode—similar to the use of nicotinamide in positive ion mode.

The sequence of two-dimensional plasmagrams 201 and 301 reflect a circumstance where the ion mobility spectrometer 100 has operated in positive ion mode for approximately 1.41 seconds (acquiring the data for segments 1-4), and then switched to operation in negative ion mode and starting negative ion mode scans (at approximately 1.41 seconds into desorption time). Thus, the data reflected in FIGS. 2 and 3 indicate that the ion mobility spectrometer 100 has been operating in both positive ion mode and negative ion mode, and that both dopants (nitrobenzonitrile and nicotinamide) and water are present. FIGS. 2 and 3 are part of an explosives-swab mode analysis. The two-dimensional plasmagram 401 depicted in FIG. 4 is also part of the explosives-swab mode analysis, and corresponds to an averaging of segments 9-19 acquired during desorption time 3.61 seconds to 7.83 seconds in negative ion mode. In the two-dimensional plasmagram 401 depicted in FIG. 4, a nitrobenzonitrile peak 404 is less prominent than the oxygen peak 403 and a reactant peak 402 and a reactant peak 405. One difference between the circumstance resulting in the two-dimensional plasmagram 301 and the two-dimensional plasmagram 401 is that plasmagram 401 is associated with the presence of the reactant hexachlooroethane in the ion mobility spectrometer 100.

Figure 5:
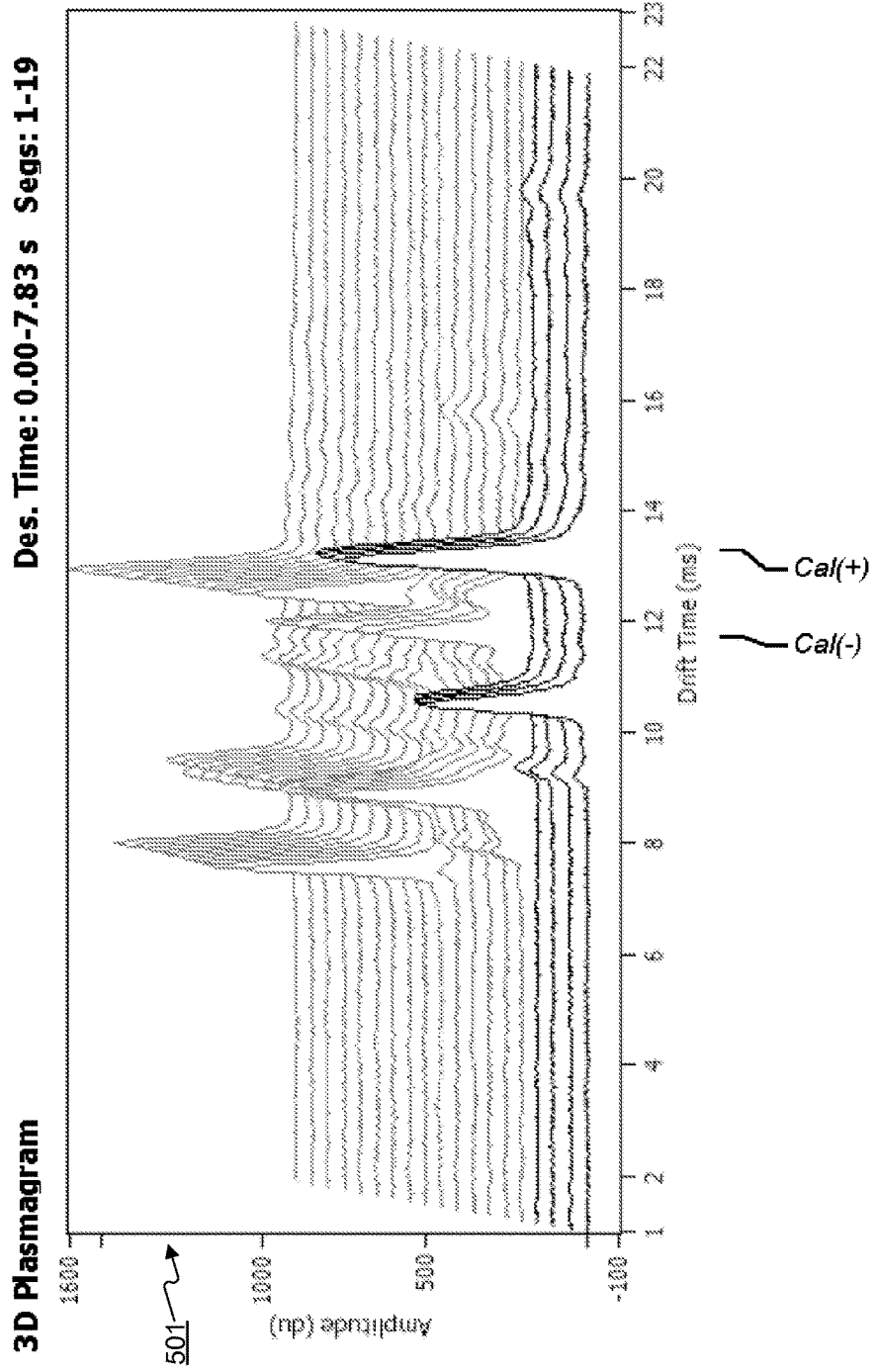
FIG. 5 depicts an example three-dimensional plasmagram associated with a first set of segment measurements in positive ion mode, negative ion mode with no reactant, and negative ion mode with reactant.

FIG. 5 depicts an example three-dimensional plasmagram 501. The three-dimensional plasmagram 501 depicts segments 1-19 (acquired during desorption time 0 seconds to 7.83 seconds) corresponding to the explosives-swab mode analysis of FIGS. 2-4. The three-dimensional view depicted in FIG. 5 reflects the pattern depicted in FIGS. 2-4: positive ion mode depicted near the abscissa (segments 1-4) corresponding to the two-dimensional plasmagram 201 in FIG. 2; negative ion mode with no reactant (segments 5-8) corresponding to the two-dimensional plasmagram 301 in FIG. 3; and negative ion mode with reactant added (segments 9-19) corresponding to the two-dimensional plasmagram 401 in FIG. 4.

Figure 6:
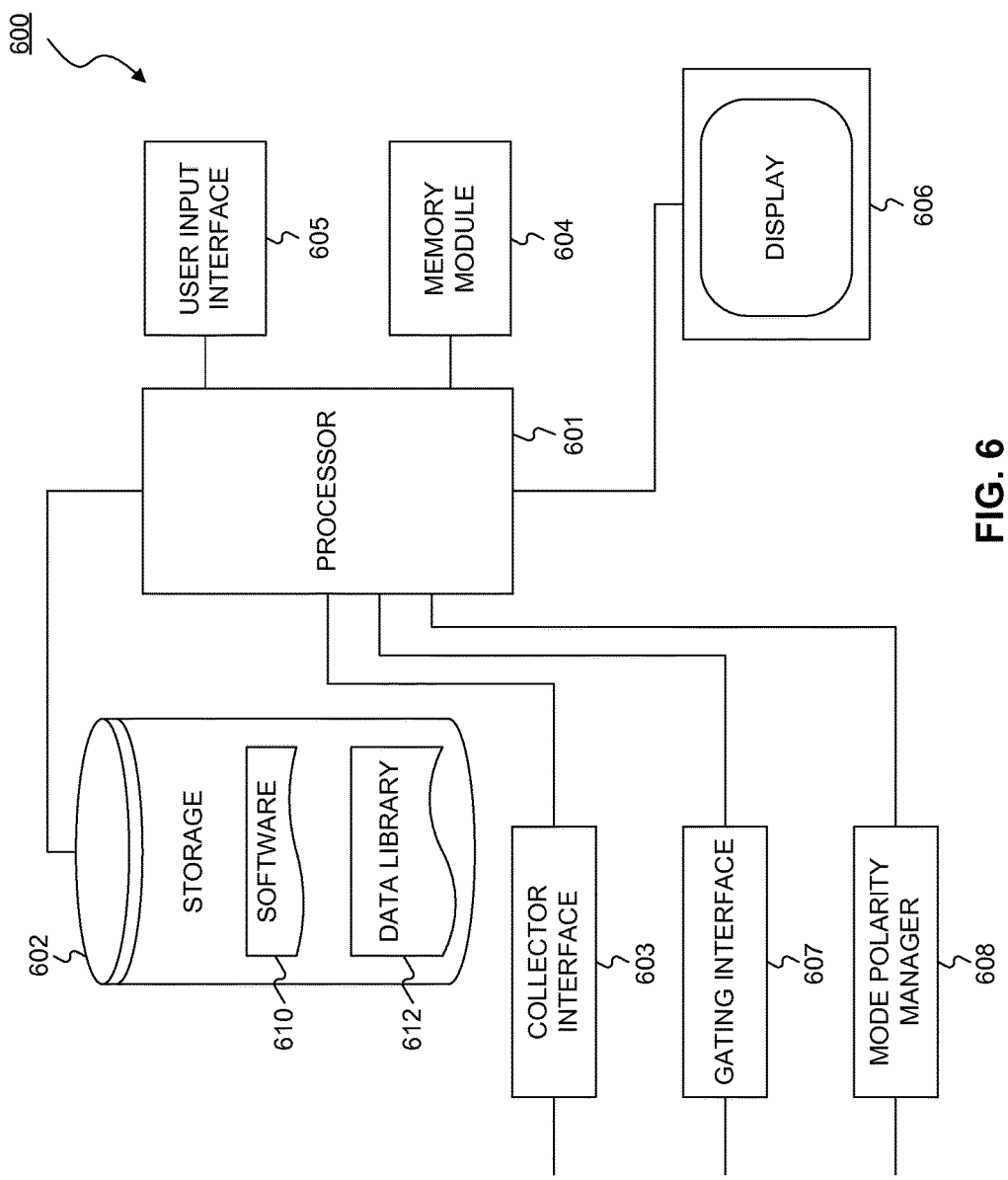
FIG. 6 depicts a data processing system consistent with an embodiment.

Consistent with an embodiment, the ion mobility spectrometer 100 includes a data processing system 600, such as a computer configured to execute a program of instructions. FIG. 6 is a schematic diagram of the data processing system 600. The data processing system 600 can include a processor 601, a memory module 604, a collector interface 603, a storage 602, a user input interface 605, a display 606, a gating interface 607, and a mode polarity manager 608. The data processing system 600 can include additional, fewer, and/or different components than those listed above. The type and number of listed devices are exemplary only and not intended to be limiting.

The processor 601 can be a central processing unit ("CPU") and/or a graphic processing unit ("GPU"). The processor 601 can execute computer program instructions to perform various processes that will be explained in greater detail below. The memory module 604 can include, among other things, a random access memory ("RAM") and a read-only memory ("ROM"). The computer program instructions can be accessed and read from the ROM, the storage 602 (such as a software 610), or any other suitable memory location, and loaded into the RAM for execution by the processor 601. Although the software is depicted as being stored on storage 602, e.g., a hard drive, the instructions comprising the software may be stored on a wide variety of tangible storage media. It is the intention of this disclosure to encompass such variations. In embodiments, computer program instructions may be embodied in a variety of media, e.g., tangible media. Depending on the type of data processing system 600 being used, the processor 601 can include one or more processors included on printed circuit boards, and/or microprocessor chips.

Collector interface 603 can be configured to receive signals from the collector 170 so the processor 601, for example, may store data representing the signals output by the collector in the storage 602.

The storage 602 can include any type of storage suitable for storing information. For example, the storage 602 can include one or more hard disk devices, optical disk devices, or any other storage devices that can retain the data. In an embodiment, the storage 602 can store data related to the data processing process, such as the scan data received from the collector 170, and any intermediate data created during the data processing process. The storage 602 can also include analysis and organization tools for analyzing and organizing the information contained therein, such as a data library 612 that can include data associated with plasmagram peak positions, peak amplitudes, peak widths, and/or reduced ion mobility values. In addition, the gating interface 607, via the hardware included in the data processing system can be configured to provide a signal, such as a pulse, to open the gating grid 145.

A user may implement the user input interface 605 to input information into the data processing system 600, and can include, for example, a keyboard, a mouse, a touch screen, and/or optical or wireless computer input devices (not shown). The user can input control instructions via the user input interface 605 to control the operation of the ion mobility spectrometer 100. For example, the user can input parameters to adjust the operation of the data processing system 600 and/or the ion mobility spectrometer 100.

The mode polarity manager 608 can be configured to manage the various voltages associated with components of the ion mobility spectrometer 100, such as the repelling grid 125, the fixed grid 135, the gating grid 145 (in closed mode, for example), the drift rings 160, and the guard grid 175. The mode polarity manager 608 can be configured to control when and in what order the various components change polarities as the ion mobility spectrometer 100 changes modes.

One or more modules of the data processing system 600 can be used to implement, for example, an automated analysis of selected peaks that can appear in the plasmagram data for the purpose of monitoring the accuracy of the ion mobility spectrometer 100. The data processing system 600 can process the plasmagram data, both in preparing plasmagram data for display as a result of sample analysis, as well as for evaluating the values of certain metrics associated with the plasmagram data. If the data processing system 600 determines that the value of certain metrics associated with a set of plasmagram data reflects a circumstance where the accuracy of the ion mobility spectrometer 100 is potentially outside an acceptable range, an alerted can be issued. If necessary, and in response to such an alert, the ion mobility spectrometer 100 can be cleaned and/or serviced. Further, the storage 602 can be used, for example, to store data relating to a detection library (such as in the data library 612), which can include characteristics of plasmagram peaks of known materials and/or other data such as reduced ion mobility values. The storage 612 can also be used, for example, to store timing information relating to switching frequencies or clear-down periods consistent with embodiments.

As described herein, selected peaks associated with plasmagram data can be analyzed based on drift time, intensity, width, and shape. In one embodiment, the selected peaks to be analyzed can be background peaks, such as those peaks associated with dopants, reactants, or other substances. Metric ranges can be preset and/or derived based on the demands and tolerances of the customer and the materials being detected.

Suitable measurements include, but are not limited to, drift time, intensity, width and shape of the plasmagram, specific metrics such as (1) a major peak associated with the hexachloroethane reactant that is doped into the IMS spectrometer; (2) a shape (e.g., the presence or absence of a tail) on the hydronium peak; and (3) the presence of certain peaks that derive from fingerprint oils.

Figure 7:
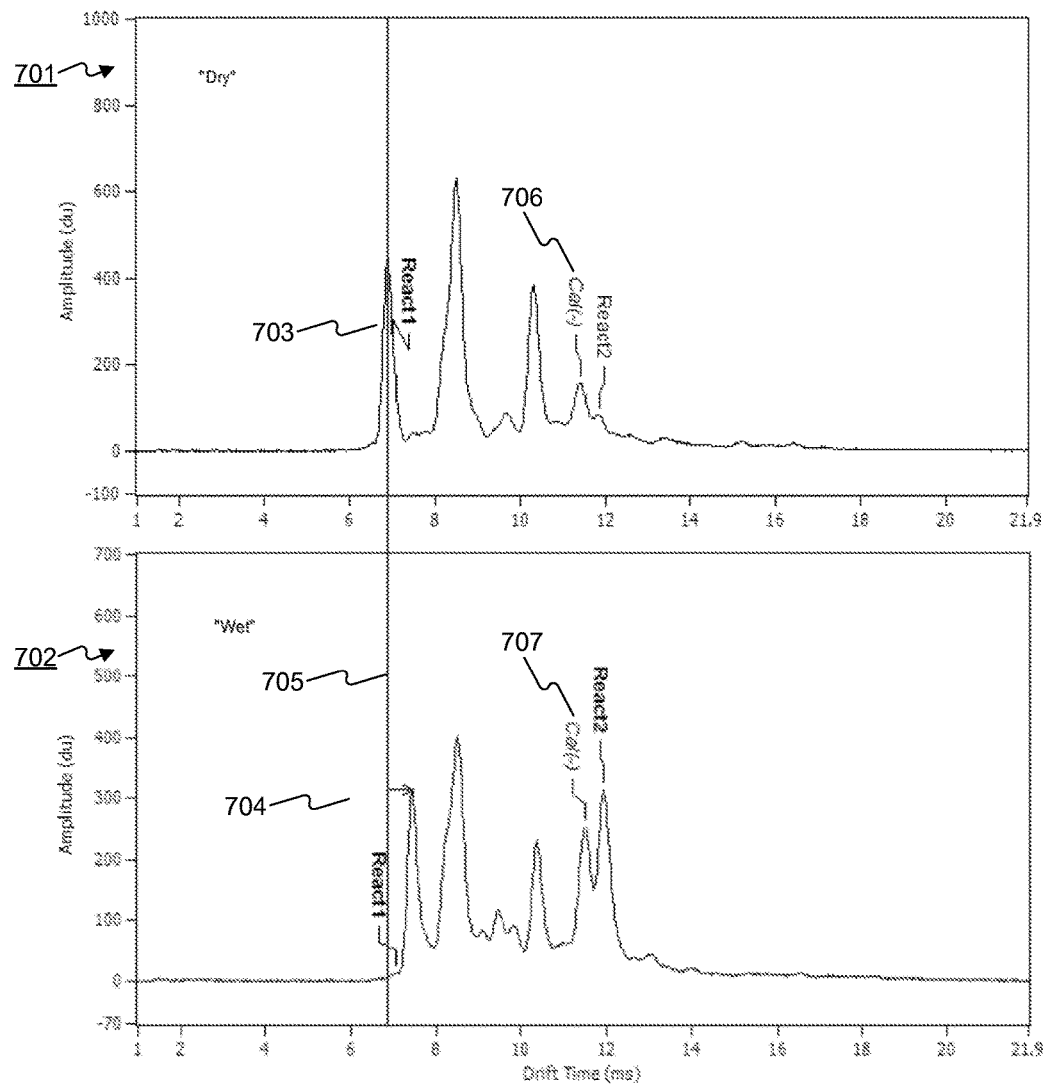
FIG. 7 depicts an example two-dimensional plasmagram showing the effect that atmospheric conditions can have on a plasmagram.

That is, a first metric can address the drift time of the major peak associated with the hexachloroethane reactant that is doped into the spectrometer. FIG. 7 depicts the effect that atmospheric conditions (e.g., temperature, humidity, etc.) can have on a plasmagram. Under dry conditions, such as those experienced in low temperatures (e.g., less than about 0° C.) or at low relative humidity (e.g., less than about 10% relative humidity at room temperature), with low water content (which typically can be less than 1 g/m3 of moisture), such as might be exhibited in a heated building during winter, the peak associated with reactant hexachloroethane has a shorter drift time than the corresponding peak under conditions with much higher water content (e.g., about 28% relative humidity at 55° C., and about 27 g/m3 of moisture). FIG. 7 depicts a plasmagram 701 which was recorded at relatively low humidity, under dry conditions. As moisture levels in the detector increase, the reactant peak 703 shifts to a reactant peak 704 in the plasmagram 702 with a larger average drift time. A line 705, superimposed on both the plasmagram 701 and the plasmagram 702, corresponds to a drift time of approximately 7 milliseconds, and illustrates the relative shift from the reactant peak 703 to the reactant peak 704.

Another illustration of the effect of the atmospheric conditions described above is the relative reduction in the measured amplitude associated with the dopant peak 706 in the plasmagram 701 from the dopant peak 707 in the plasmagram 702. Although the ordinate in the plasmagram 701 has a broader range than the ordinate in the plasmagram 702, it can be seen that the dopant peak 706 in the plasmagram 701 is less than approximately 200 units, while the dopant peak 707 in the plasmagram 702 is above 200 units.

A metric associated with the relative position of the reactant peak 703 and the amplitude of the dopant peak 706 can be used to monitor the health of a consumable Air Purification Cartridge (APC) 115 in the ion mobility spectrometer 100. If reactant peak 703 moves out of the expected drift time range to longer drift times this can be an indication that the APC is no longer drying the drift gas effectively (e.g., it is expiring or has expired). An exemplary listing of drift times under various conditions is shown in table 1 below. (The reference pressure for the sample data is 101.21 kPa.)

TABLE 1

| Condition | K0 | Variability (µs) | Calculated Drift Time (ms) | Lowest Normal Drift Time (ms) | Highest Normal Drift Time (ms) |
| --- | --- | --- | --- | --- | --- |
| "Dry" | 2.733 | 65 | 6.779 | 6.714 | 6.844 |
| "Moderate" | 2.6767 | 120 | 6.922 | 6.802 | 7.042 |
| "Wet" | 2.5769 | 200 | 7.190 | 6.990 | 7.390 |

Figure 8:
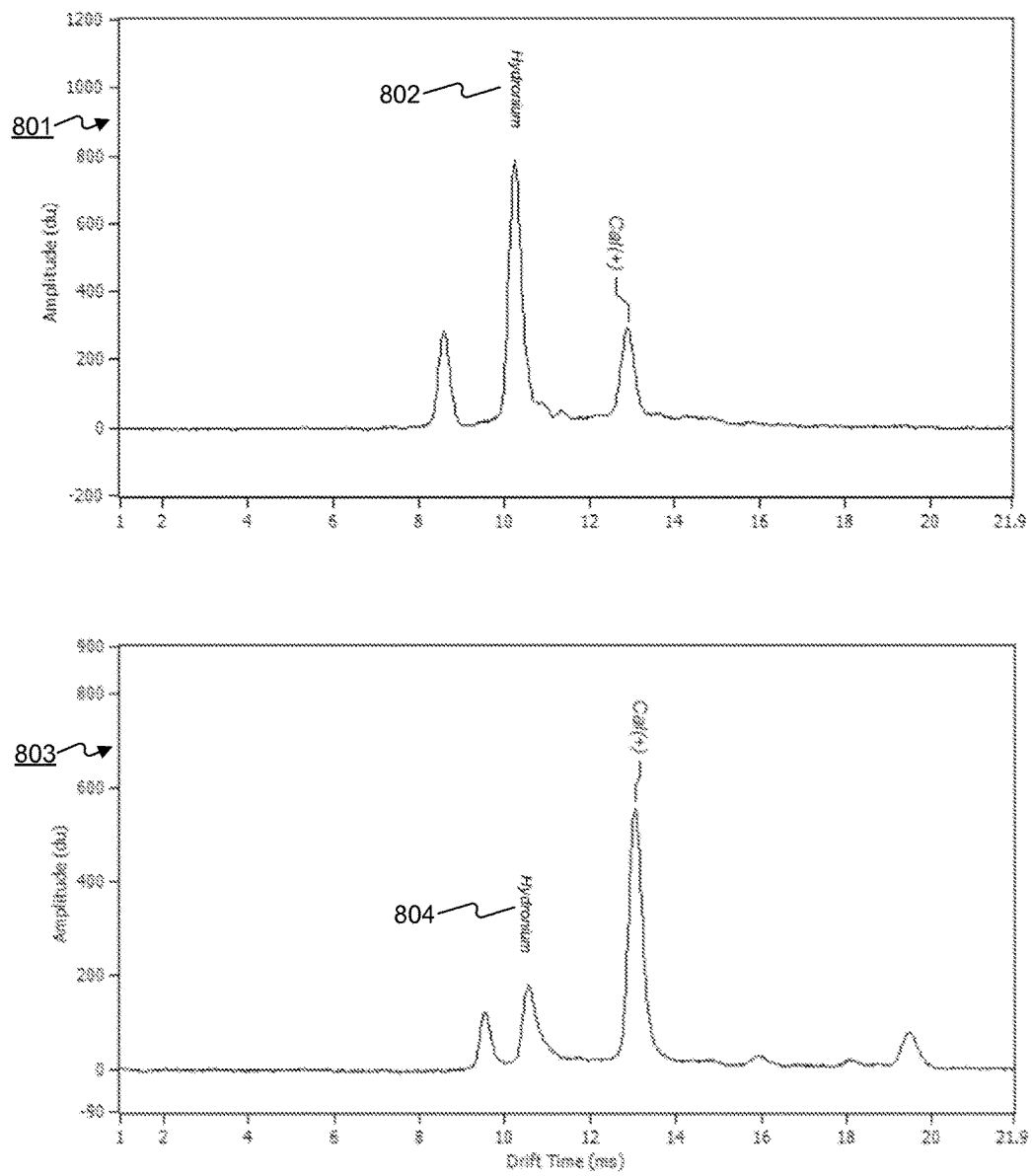
FIG. 8 depicts an example two-dimensional plasmagram showing the effect of atmospheric conditions on the hydronium peak.

A second metric can address the shape (e.g., the presence or absence of a tail) on the hydronium peak or oxygen peak. An example of this can be the presence or absence of a tail, a shoulder, or other shift. FIG. 8 depicts the effect of atmospheric conditions on the hydronium peak 802. In FIG. 8, the plasmagram 801 depicts the hydronium peak 802 under dry conditions, which exhibits an amplitude of approximately 800 d.u. (digital units) and a drift time of 10 milliseconds. The plasmagram 803 depicts the hydronium peak 804 under wet conditions, which exhibits an amplitude of approximately 200 d.u. and a drift time of 10.5 milliseconds. Thus, the hydronium peak 802 may be suppressed, shifted or develop a tail such that the average of the hydronium peak 802 exhibits a longer drift time, any of which can be an indicator of the presence of moisture or other contaminants. The oxygen peak can also be altered by the presence of moisture, carbon dioxide or reactant. For example, the behavior of the oxygen peak can be analogous to the behavior of the reactant peak in FIG. 7, but the effect is less pronounced. It is possible to use these metrics both on-the-fly and in post-collection troubleshooting. The behavior of background peaks can provide information relating to potential causes of faults. As another example, the detected presence of a reactant peak in plasmagrams generated by an ion mobility spectrometer 100, where the addition of the associated reactant is not enabled, can be an indication of faults within the flow system of the ion mobility spectrometer 100.

A third metric can address the presence of certain peaks that commonly occur in samples collected in the field; for example substances found in the environment, in fingerprint oils and personal care products. Over time the build-up of substances such as finger print oils can lead to modification of readings of the ions of interest within the drift region 165. However, because these ions are easily identifiable by their characteristic in the plasmagram, the ion mobility spectrometer 100 may be configured to account for such substances (such as by preliminarily removing any peaks associated with such substances prior to the display of the results of an analysis to a user). Even though plasmagram peaks associated with such substances may be suppressed before providing an output, the underlying data are available to analyze for purposes of monitoring the health of the ion mobility spectrometer 100.

Figure 9:
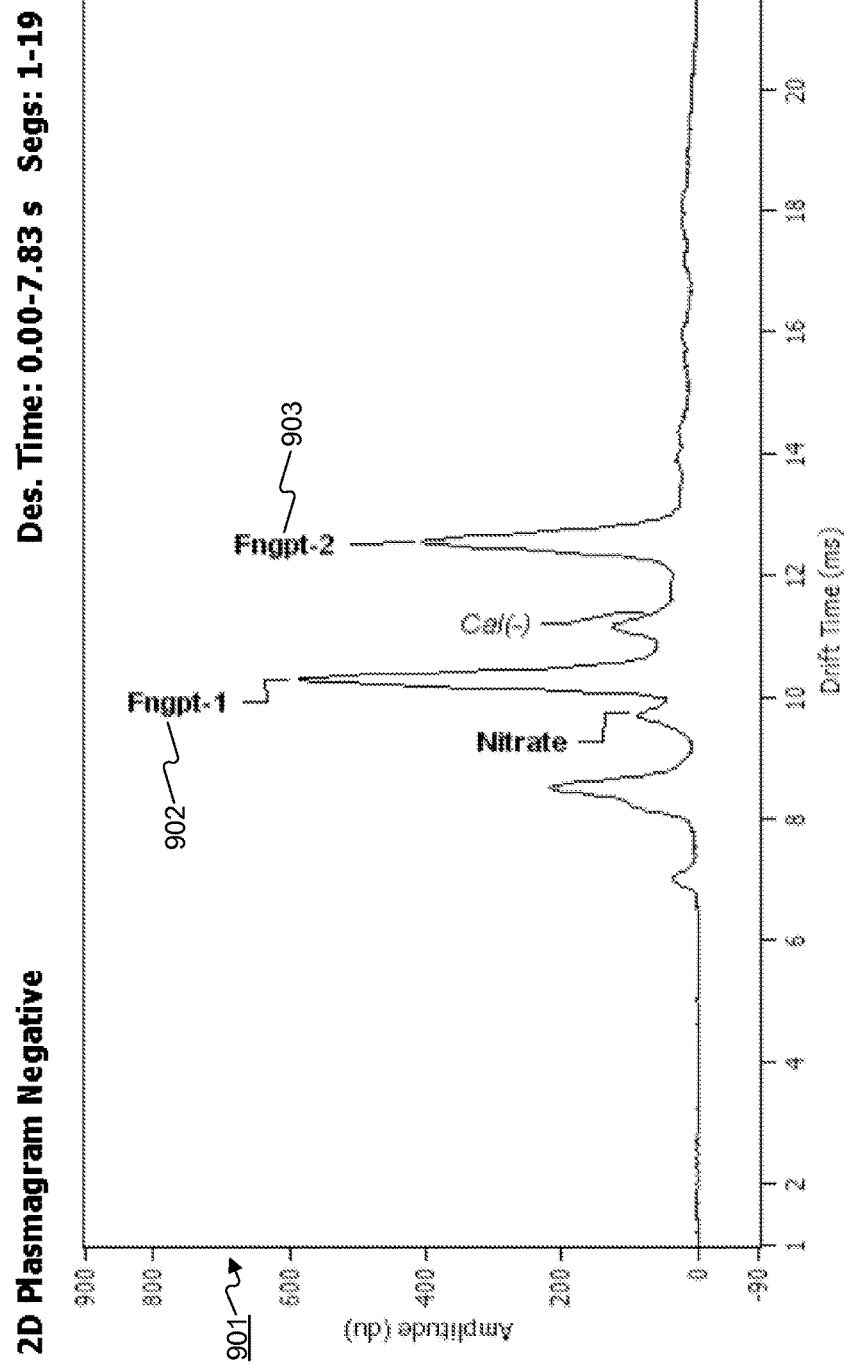
FIG. 9 depicts an example two-dimensional plasmagram showing the presence of fingerprint oils.

FIG. 9 depicts a plasmagram 901 containing a plasmagram peak 902 and a plasmagram peak 903 corresponding to the presence of fingerprint oils. Although the plasmagram peak 902 and the plasmagram peak 903 both correspond to fingerprint oils, they exhibit different amplitudes due to the possible variations in fingerprint oils. In an embodiment, the presence of fingerprint oils can be used as a diagnostic metric. By way of example, only, the peak 903 can be larger than peak 902 in FIG. 9. Even under this scenario, the presence of peak 903 would still be indicative of the presence of fingerprint oils and considered when evaluating the data metric, as would be the case if only peak 902 were present.

Figure 10:
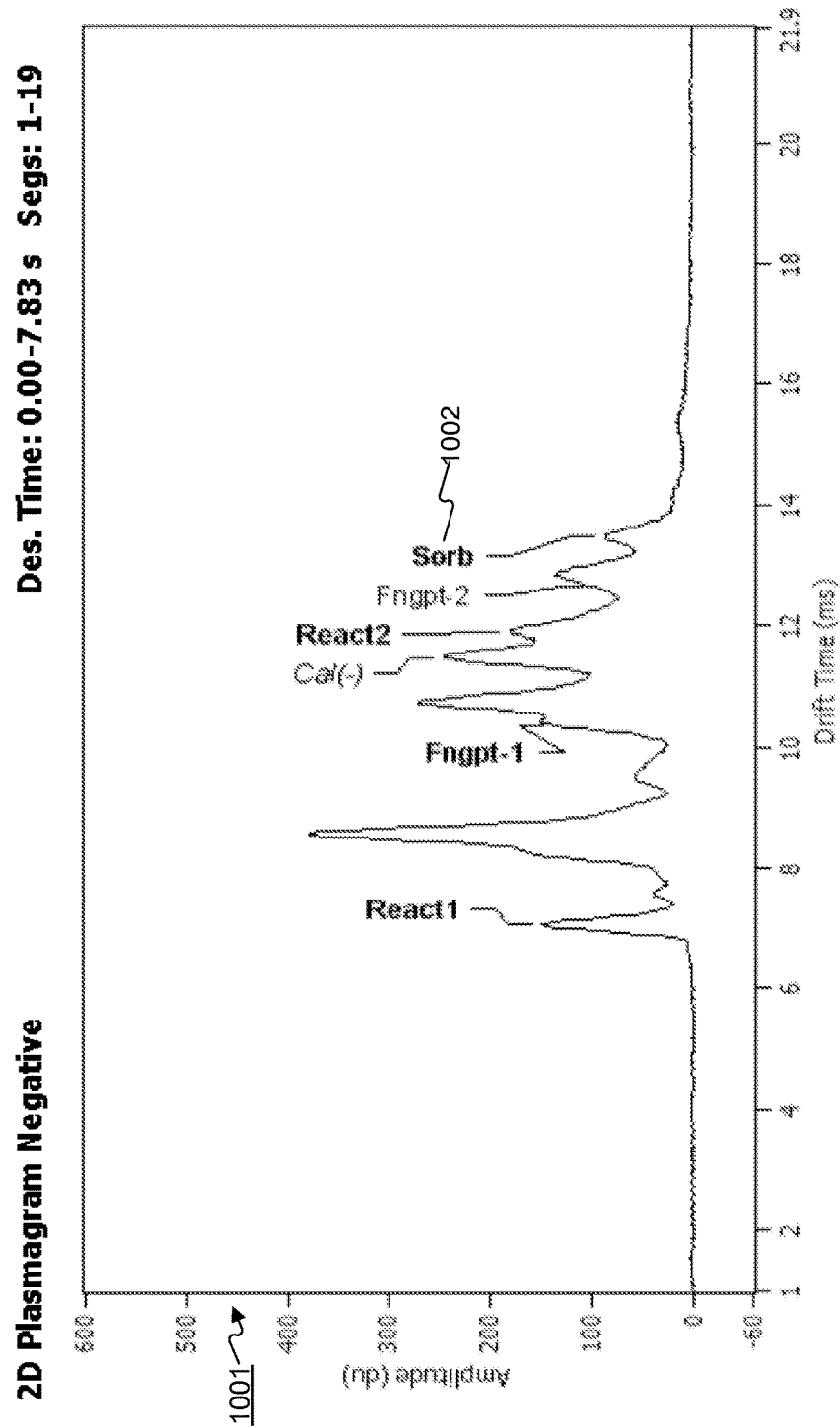
FIG. 10 depicts an example two-dimensional plasmagram showing the presence of sorbitols.
Figure 11:
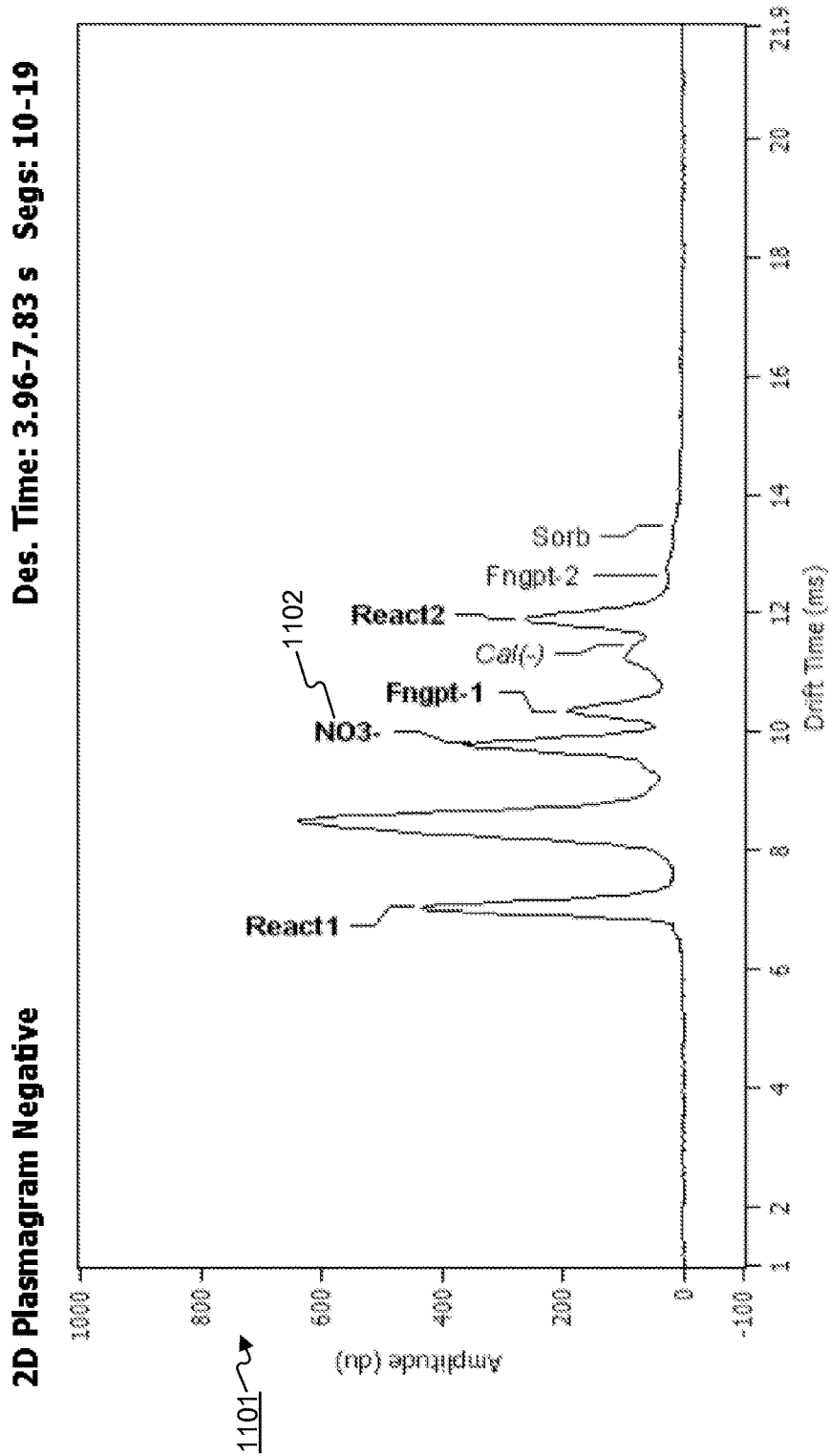
FIG. 11 depicts an example two-dimensional plasmagram showing the presence of nitrates.

Other materials and substances that are part of the environment can also contribute recognizable peaks in the plasmagram. FIG. 10 depicts plasmagram 1001 showing another background contaminant, sorbitol, represented by plasmagram peak 1002. Sorbitol is a sugar found in many personal care products such as hand lotions. FIG. 11 depicts plasmagram 1101 showing another background contaminant, nitrates, represented by plasmagram peak 1102. Nitrates are generally present in field backgrounds—albeit in small amounts. When nitrates accumulate to certain levels, however, they can prevent accurate peak readings. The presence of certain background peaks may be used to diagnose problems when troubleshooting an instrument, or to modify the detection algorithm to ensure that the detector correctly identifies target substances.

Figure 12:
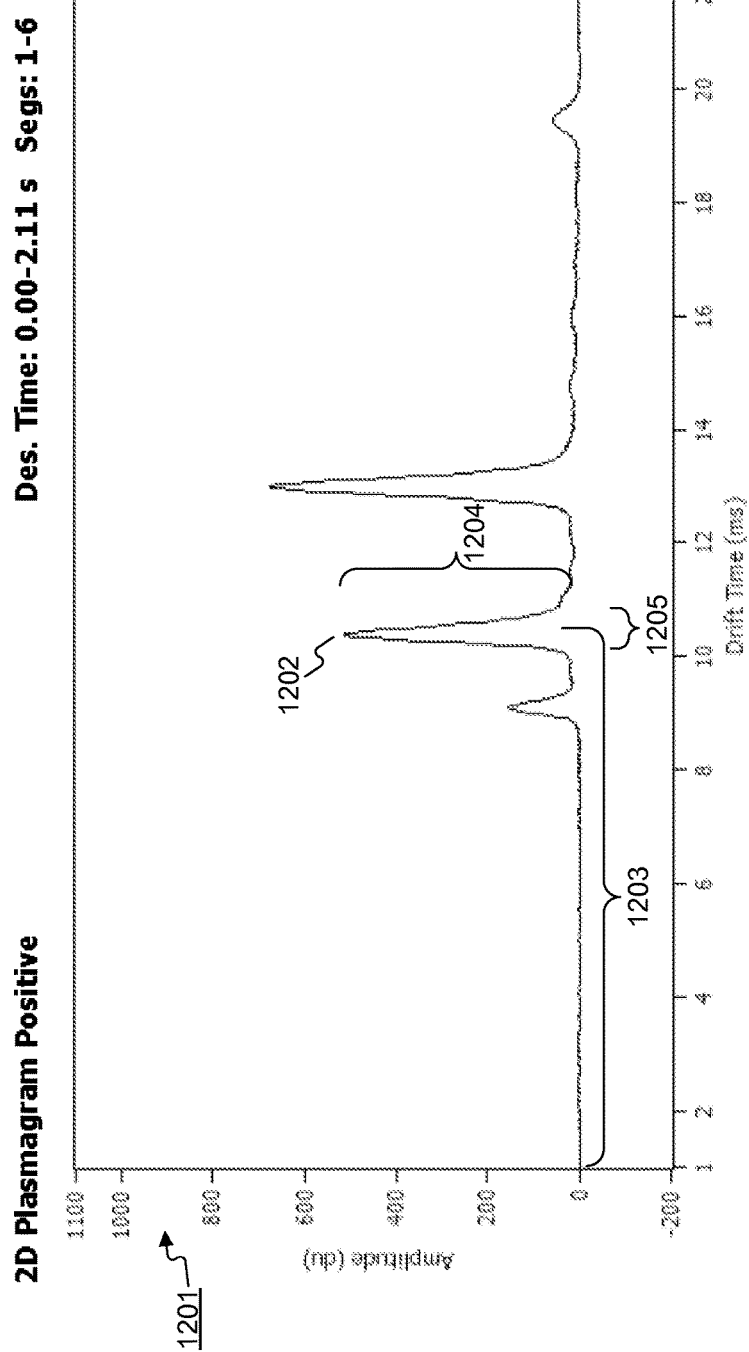
FIG. 12 depicts an example two-dimensional plasmagram showing a plurality of plasmagram characteristics.

Other plasmagram characteristics which could be analyzed for being out of a predetermined range are illustrated by FIG. 12. FIG. 12 is a depiction of a plasmagram 1201 having a plurality of plasmagram peaks. For illustration and discussion purposes, we consider one plasmagram peak 1202. The plasmagram peak 1202 has a drift time 1203 which is measured in milliseconds, as listed on the abscissa. The drift time 1203 corresponds to the amount of time the ions corresponding to the plasmagram peak 1202 took to travel from the ionization region 140 to the collector 170 after the gating grid 145 pulse allowed them to enter the drift region 165. As discussed above, the drift time is a function of the ion mobility. Drift time is one metric of a plasmagram which can be measured and compared consistent with the present disclosure. Further, the plasmagram peak 1202 has an amplitude 1204 which is measured in arbitrary (relative) units known as digital units (d.u.). The amplitude of a particular plasmagram peak corresponds roughly (or relatively) to the number of ions which reached the collector 170 at that particular drift time. The more ions reach the collector 170, the more current will be created at the collector 170 and hence the higher the amplitude 1204 of the plasmagram peak 1202. Amplitude is another metric of a plasmagram which can be measured and compared consistent with the present disclosure. Further, the plasmagram peak 1202 has a width 1205. Since there is some variation in ion mobility even among a single ionic species, the width 1205 of the plasmagram peak 1202 can corresponds roughly (or relatively) to the number of ions which reached the collector 170 at that particular drift time. A large number of a particular type of ion will correlate to a plasmagram peak having a large amplitude and a large width. Width is another metric of a plasmagram which can be measured and compared consistent with the present disclosure. In addition to drift time, amplitude and width, a plasmagram peak can be said to have a shape which may form when two plasmagram peaks begin to merge into a distinctive shape. Shape is another metric of a plasmagram which can be measured and compared consistent with the present disclosure. Although the above discussion relates to the plasmagram peak 1202, other plasmagram peaks, or in some cases each combination of plasmagram peaks, in the plasmagram may possesses a drift time, amplitude, a width, and a shape.

Continuous monitoring of one or more of the metrics described herein can occur with the recorded plasmagram.

Figure 13:
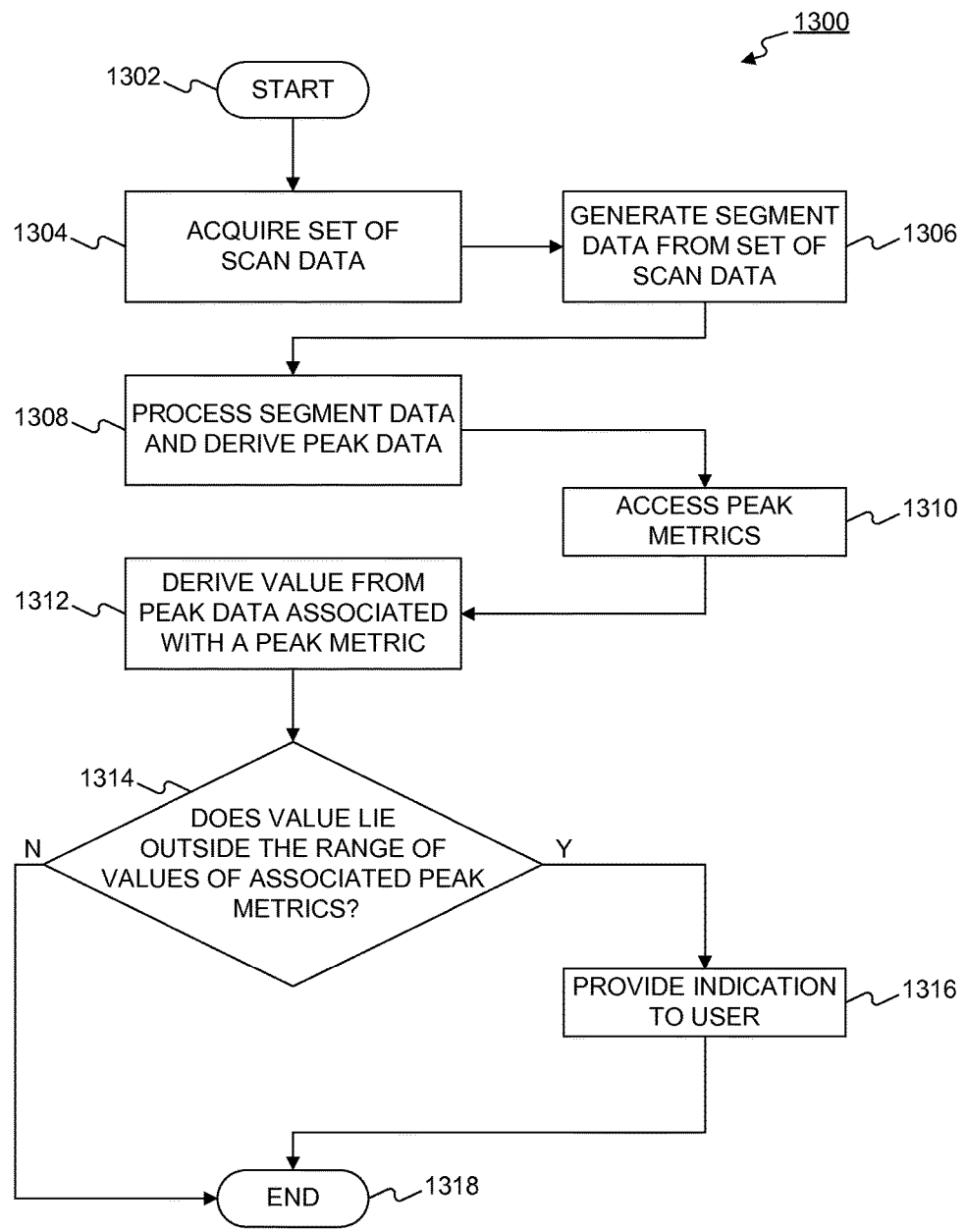
FIG. 13 is a flowchart depicting a method of monitoring an ion mobility spectrometer consistent with an embodiment.

In one embodiment, illustrated in FIG. 13, the ion mobility spectrometer 100 can provide an indication to a user upon a determination that certain peak metrics associated with background peaks are outside of a range of values, such as exceeding a certain size or being less than a certain size, occurring at a certain position, and/or exceeding a certain width. Such peak metrics can indicate that the ion mobility spectrometer 100 is due for maintenance.

Step 1304 corresponds to the acquisition of scan data by the ion mobility spectrometer 100. Data corresponding to a single scan can be acquired by operation of the ion mobility spectrometer in either positive ion mode or negative ion mode as described above. In addition, as has been discussed earlier, an exemplary time period for such a single scan can be 25 milliseconds. A set of scan data can correspond to a plurality of such scans. Data corresponding to the scan data acquired in step 1304 may be conveyed to the processor 601 through the collector interface 603.

In step 1306, segment data is generated from the set of scan data acquired in step 1304. For example, a plurality of scans can be co-added to form a single segment. The operation associated with step 1306 can reduce the signalto-noise associated with the acquisition of scan data and can be performed by the processor 601 in accordance with instructions loaded into the memory module 604 from the storage 602.

In step 1308, the segment data generated in step 1306 can be processed by the processor 601 to identify any characteristics of the segment data that can correspond to peak metrics associated with reactants, dopants, contaminants, etc. Again, this operation can be performed by the processor 601 in accordance with signal processing instructions loaded into the memory module 604 from the storage 602. Without limitation, a set of peak metrics of the segment data generated by the ion mobility spectrometer 100 that can be derived include the amplitude of a peak in the segment data at a particular drift time in positive ion mode or negative ion mode, the full-width-half-maximum of a peak in the segment data at a particular drift time (in positive ion mode or negative ion mode). Other example peak metrics can include the difference between the observed peak drift time and the expected peak drift time based upon the observed drift time of a calibrant peak.

In step 1310, the processor 601 can access a library of peak metrics. The data library 612 can contain a collection of information relating to such peak metrics. For example, the data library 612 may include a data collection, stored in a lookup table or some other tabular form, a plurality of drift times cross-referenced to peak amplitudes, peak full-width-at-half-maximum ("FWHM"), positive ion mode or negative ion mode, etc. Such information can be used to derive a value from the peak data associated with the acquired segment data, and that can be expected to correspond to a particular peak metric (step 1312).

For example, ions associated with hexachloroethane, hydronium, fingerprint oils, sorbitols, and/or nitrates can be present in the ion mobility spectrometer 100 in a scan (i.e., positive ion mode or negative ion mode) as background. Accordingly, at step 1314, processor 601 can determine whether the generated segment data according to one of a positive ion mode or a negative ion mode exhibits a peak metric (such as a certain amplitude, width, etc.) at a drift time corresponding to hexachloroethane, hydronium, fingerprint oils, sorbitols, and/or nitrates etc. If the segment data indicates a value of the peak metric associated with the peak data in the appropriate ion mode, and the value of the peak metric is outside of a certain range, processor 601 can generate instructions associated with providing an indication to a user that the ion mobility spectrometer 100 may need servicing (step 1316). Other peak metrics than can be used to determine whether the ion mobility spectrometer needs servicing can include the absence of a peak in the appropriate ion mode and/or FWHM of a peak that is too large.

If processor 601 determines that the value from the peak data associated with a peak metric is within a range of values, then the ion mobility spectrometer 100 can continue operation without providing an indication to a user that the ion mobility spectrometer 100 requires servicing (indicated by step 1318). In addition, and in connection with step 1316 described above, processor 601 can also provide an option for a user to select a clear-down operation, such as a fast-switching clear-down. For example, ion mobility spectrometer 100 can be configured to provide an indication, through the display 606, that servicing is required and/or that a clear-down operation may be warranted. The ion mobility spectrometer 100 can further provide as an option to the user the ability to select the clear-down option and implement fast clear-down.

Figure 14:
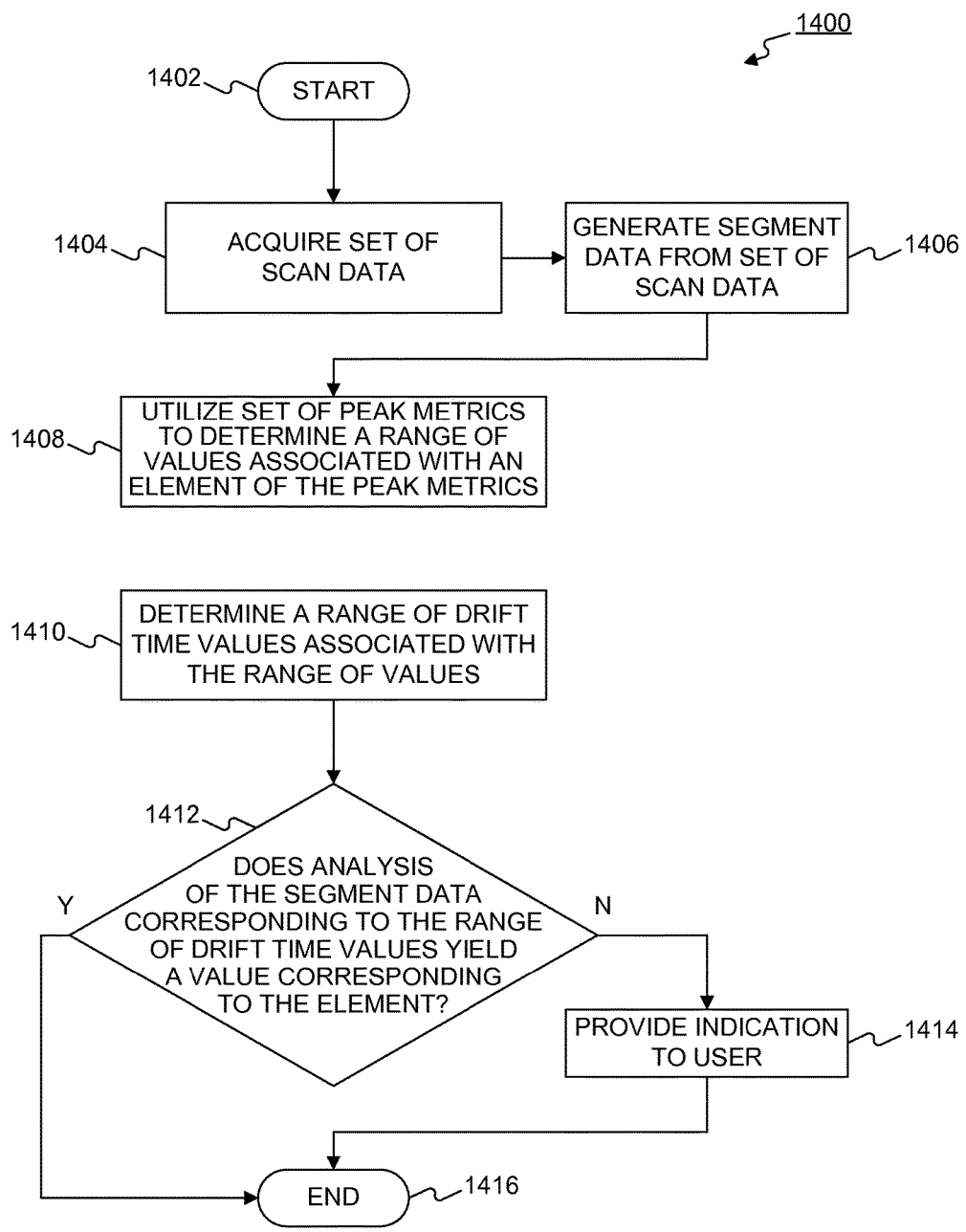
FIG. 14 is a flowchart depicting a further method of monitoring an ion mobility spectrometer consistent with an embodiment.

In a further embodiment, illustrated in FIG. 14, the ion mobility spectrometer 100 can provide an indication to a user upon a determination that the segment data does not yield a value associated with a certain peak metric, such as an amplitude value associated with a particular reactant, dopant, or contaminant. Again, such a result can indicate that the ion mobility spectrometer 100 is due for maintenance.

Step 1404 corresponds to the acquisition of scan data by the ion mobility spectrometer 100. Data corresponding to a single scan can be acquired by operation of the ion mobility spectrometer in either positive ion mode or negative ion mode as described above. In addition, as has been discussed earlier, an exemplary time period for such a single scan can be 25 milliseconds. A set of scan data can correspond to a plurality of such scans. Data corresponding to the scan data acquired in step 1404 may be conveyed to the processor 601 through the collector interface 603.

In step 1406, segment data is generated from the set of scan data acquired in step 1404. For example, a plurality of scans can be co-added to form a single segment. The operation associated with step 1406 can reduce the signal-to-noise associated with the acquisition of scan data and can be performed by the processor 601 in accordance with instructions loaded into the memory module 604 from the storage 602.

In step 1408, the processor 601 can access a set peak metrics. The data library 612 can contain a collection of information relating to such set of peak metrics. For example, the data library 612 may include a data collection, stored in a lookup table or some other tabular form, a plurality of drift times cross-referenced to peak amplitudes, peak FWHM, positive ion mode or negative ion mode, etc. Such information can be used to derive a range of values associated with an element of the set of peak metrics (step 1408).

For example, ions associated with hexachloroethane, hydronium, fingerprint oils, sorbitols, and/or nitrates can be present in the ion mobility spectrometer 100 in a scan (e.g., positive ion mode or negative ion mode) as background. Accordingly, at step 1410, the processor 601 can determine a range of drift time values according to one of a positive ion mode or a negative ion mode associated with a peak metric (such as an a certain amplitude, width, etc.). If analysis of the segment data over the appropriate drift time does not indicate the presence of a value of the peak metric in the appropriate ion mode (step 1412), the processor 601 can generate instructions associated with providing an indication to a user that the ion mobility spectrometer 100 may be due for servicing (step 1414).

For example, ions associated with hexachloroethane, hydronium, fingerprint oils, sorbitols, and/or nitrates can be present in the ion mobility spectrometer 100 in any appropriate scan (e.g., positive ion mode or negative ion mode) as background. Accordingly, at step 1412, the processor 601 can determine whether the generated segment data according to one of a positive ion mode or a negative ion mode exhibits a value associated with a peak metric (such as an a certain amplitude, width, etc.) at a drift time corresponding to hexachloroethane, hydronium, fingerprint oils, sorbitols, and/or nitrates etc. Again, if analysis of the segment data does not indicate a value corresponding to the peak metric, the processor 601 can generate instructions associated with providing an indication that the ion mobility spectrometer 100 may need servicing (step 1414). Consistent with the current disclosure, other peak metrics than can be used to determine whether servicing is appropriate, examples include but are not limited to a FWHM that is too large.

If the processor 601 determines that the set of segment data yields a value corresponding to the peak metric, then the ion mobility spectrometer 100 can continue operation without providing an indication that the ion mobility spectrometer requires servicing (indicated by step 1416). Alternatively, and upon deriving a value associated with the peak metric, the processor 601 can continue according to steps 1314, 1316, and 1318 as described in connection with FIG. 13 above.

In addition, and in connection with step 1414 as described above, the processor 601 can also provide an option to select a clear-down operation, such as a fast clear-down. For example, the ion mobility spectrometer 100 can be configured to provide an indication, through the display 606, that servicing is appropriate and/or that a clear-down operation may be warranted. The ion mobility spectrometer 100 can further provide as an option to the user the ability to select the clear-down option and implement fast clear-down.

Generally, the respective sets of segment data in the ion mobility spectrometer 100 can be analyzed by a detection routine (which can be stored, for example, in firmware) and which can be configured to search for target analytes. Consistent with one embodiment, the ion mobility spectrometer 100 can also be configured to check the status of reactants, dopants, contaminants, etc.—any background substance. Just as with an alert associated with a target analyte, the ion mobility spectrometer can be configured to determine if one or more of the peak metrics associated with a background substance is outside a range, and—if so—generate an indication. The indication could include a description of the discrepancy and a recommended remedy; as an example, should the primary hexachloroethane peak be found to be out of range as defined in the first metric described, an operator can be prompted to replace the Air Purification Cartridge 115.

In a further embodiment, the ion mobility spectrometer 100 can also be configured to acquire and store data associated with background peaks for diagnostic purposes. For example, and without limitation, the ion mobility spectrometer 100 can be programmed to provide an alert in the event that a specified background peak is identified as occurring in a segment data set. However, the ion mobility spectrometer 100 can be configured to monitor a specified background peak without triggering an alarm. Ion mobility spectrometer 100 can be programmed to monitor background peaks of interest, such as the reactant, oxygen and fingerprint peaks, in such a way as to avoid satisfying the alarm logic—thereby ensuring that the background peaks can be identified in the plasmagram, but cannot trigger an alarm on the ion mobility spectrometer 100.

For example, the alarm logic associated with the ion mobility spectrometer 100 can be configured to trigger a "Health Check" alarm in the event that the segment data set associated with FIG. 2, and FIG. 3, and FIG. 4 are based on the presence of the Reactl peak (peak 402). However, because the segment data set associated with FIG. 2 (positive ion mode) is not expected exhibit any overlap with the segment data set associated with FIG. 4 (negative ion mode with reactant), the alarm logic will not be satisfied. Even though the alarm logic will not be satisfied, the specified background peak will be identified in each plasmagram, but the "HealthCheck" alarm will not be triggered.

Other embodiments of the invention will be apparent to those skilled in the art from consideration of the specification and practice of the embodiment disclosed herein. Although one or more methods have been described in conjunction with the ion mobility spectrometer 100, it is to be apparent that the method may be used with other devices and configurations of ion mobility spectrometers. It is intended that the specification and examples be considered as exemplary only, with a true scope and spirit of the invention being indicated by the following claims.

We claim:

1. A method of monitoring an ion mobility spectrometer, comprising:
   acquiring ion mobility spectrometer scan data;
   generating a segment data set from the ion mobility spectrometer scan data;
   obtaining a set of peak metrics from the segment data;
   utilizing the set of peak metrics to determine a range of values associated with a criteria element of the set of peak metrics;
   determining a range of segment drift time values associated with the range of values; and
   in the event that analysis of a subset of the segment data corresponding to the range of segment drift time values does not yield a value corresponding to the range of values executing at least one of:
   (a) providing an indication that the ion mobility spectrometer requires clear-down;
   (b) triggering clear-down of the ion mobility spectrometer;
   (c) providing an indication that an alternative detection algorithm should be implemented; or
   (d) triggering an alternative detection algorithm.

2. The method of monitoring of claim 1, wherein the criteria element comprises an amplitude.

3. The method of monitoring of claim 2, further comprising: determining that an element of a set of amplitude values associated with the subset of segment data is less than the range of values.

4. The method of monitoring of claim 1, wherein the criteria element comprises a peak width.

5. The method of monitoring of claim 4, further comprising: determining that an element of a set of peak width values associated with the subset of segment data is more than the range of values.

6. The method of monitoring of claim 1, wherein the set of peak metrics is associated with at least one of: a reactant, hydronium, or a dopant.

7. The method of monitoring of claim 6, wherein the dopant comprises hexachloroethane.

8. The method of monitoring of claim 1, wherein the set of peak metrics is associated with one or more of: fingerprint oil, sorbitol, or nitrate.

9. The method of monitoring of claim 1, wherein the indication that the ion mobility spectrometer requires clear-down further comprises an option to manually initiate the clear-down operation of an ion mobility spectrometer.

10. An ion mobility spectrometer analysis system comprising:
    a collector interface coupled to a collector; and
    a processor configured to:
    acquire ion mobility spectrometer scan data from the collector interface;
    generate a segment data set from the ion mobility spectrometer scan data;
    obtain a set of peak metrics from the segment data;
    utilize the set of peak metrics to determine a range of values associated with a criteria element of the set of peak metrics;
    determine a range of segment drift time values associated with the range of values, wherein the ion mobility spectrometer analysis system is configured in the event that analysis of a subset of the segment data corresponding to the range of segment drift time values does not yield a value corresponding to the criteria element to:
(a) provide an indication that the ion mobility spectrometer requires clear-down;
(b) trigger a clear-down of the ion mobility spectrometer;
(c) provide an indication that an alternative detection algorithm should be implemented; or
(d) trigger an alternative detection algorithm.

11. The ion mobility spectrometer analysis system of claim 10, wherein the criteria element comprises an amplitude.

12. The ion mobility spectrometer analysis system of claim 11, wherein the processor is further configured to determine that an element of a set of amplitude values associated with the subset of segment data is less than the range of values.

13. The ion mobility spectrometer analysis system of claim 10, wherein the criteria element comprises a peak width.

14. The ion mobility spectrometer analysis system of claim 13, wherein the processor is further configured to determine that an element of a set of peak width values associated with the subset of segment data is more than the range of values.

15. The ion mobility spectrometer analysis system of claim 10, wherein the set of peak metrics is associated with at least one of: a reactant, hydronium, or a dopant.

16. The ion mobility spectrometer analysis system of claim 15, wherein the dopant comprises hexachloroethane.

17. The ion mobility spectrometer analysis system of claim 11, wherein the set of peak metrics is associated with contamination comprises one or more of: fingerprint oil, sorbitol, or nitrate.

18. The ion mobility spectrometer analysis system of claim 11, wherein the indication comprises an option to initiate a clear-down of an ion mobility spectrometer.

19. The ion mobility spectrometer analysis system of claim 11, further comprising data storage, wherein the processor is configured to retrieve at least certain data from the data storage, and the at least certain data comprises data associated with a portion of the set of peak metrics.

20. A computer-readable medium comprising instructions stored thereon, wherein the instructions, responsive to being executed by a processor, cause the processor to perform a method comprising:
acquiring ion mobility spectrometer scan data;
generating a segment data set from the ion mobility spectrometer scan data;
utilizing a set of peak metrics to determine a range of values associated with a criteria element of the set of peak metrics; and
determining a range of segment drift time values associated with the range of values, wherein the processor is associated with an ion mobility spectrometer analysis system that is configured in event that analysis of a subset of the segment data that corresponds to the range of segment drift time values does not yield a value that corresponds to the criteria element:
(a) providing an indication that the ion mobility spectrometer requires clear-down;
(b) triggering clear-down of the ion mobility spectrometer;
(c) providing an indication that an alternative detection algorithm should be implemented; or
(d) triggering an alternative detection algorithm.

* * * * *